(12) United States Patent
Chang

(10) Patent No.: US 12,409,208 B2
(45) Date of Patent: Sep. 9, 2025

(54) TREATING TISSUE FIBROSIS WITH INTERLEUKIN 24

(71) Applicant: LBL BIOTECHNOLOGY INC., Tainan (TW)

(72) Inventor: Ming-Shi Chang, Tainan (TW)

(73) Assignee: LBL BIOTECHNOLOGY INC., Tainan (TW)

( * ) Notice: Subject to any disclaimer, the term of this patent is extended or adjusted under 35 U.S.C. 154(b) by 632 days.

(21) Appl. No.: 17/771,930

(22) PCT Filed: Oct. 28, 2020

(86) PCT No.: PCT/US2020/057781
§ 371 (c)(1),
(2) Date: Apr. 26, 2022

(87) PCT Pub. No.: WO2021/086997
PCT Pub. Date: May 6, 2021

(65) Prior Publication Data
US 2022/0378875 A1   Dec. 1, 2022

Related U.S. Application Data

(60) Provisional application No. 62/926,884, filed on Oct. 28, 2019.

(51) Int. Cl.
*A61K 38/20* (2006.01)
*A61K 39/00* (2006.01)
*A61K 39/395* (2006.01)
*A61P 11/00* (2006.01)

(52) U.S. Cl.
CPC .......... *A61K 38/20* (2013.01); *A61K 39/3955* (2013.01); *A61P 11/00* (2018.01); *A61K 2039/505* (2013.01)

(58) Field of Classification Search
CPC ................ A61K 38/20; A61K 39/3955; A61K 2039/505; A61K 2039/545; A61P 11/00; C07K 16/244
See application file for complete search history.

(56) References Cited

U.S. PATENT DOCUMENTS

| | | | | |
|---|---|---|---|---|
| 7,611,705 B2* | 11/2009 | Chang | ...................... | A61P 1/02 424/130.1 |
| 8,597,647 B1* | 12/2013 | Chang | ..................... | A61P 13/12 530/387.3 |
| 8,603,470 B1 | 12/2013 | Chang | | |
| 2005/0142108 A1 | 6/2005 | Grunig et al. | | |
| 2008/0171041 A1* | 7/2008 | Thompson | ............... | A61P 19/02 424/135.1 |
| 2011/0256093 A1 | 10/2011 | Chang | | |
| 2013/0039923 A1 | 2/2013 | Pass et al. | | |
| 2013/0315893 A1 | 11/2013 | Chang | | |

FOREIGN PATENT DOCUMENTS

| | | | |
|---|---|---|---|
| EP | 2295079 A2 | 3/2011 | |
| WO | WO-2009042798 A1 * | 4/2009 | ............. A61K 35/17 |
| WO | WO 2009/117640 A2 | 9/2009 | |
| WO | 2016083304 A1 | 6/2016 | |

OTHER PUBLICATIONS

"Pulmonary Fibrosis" Mayo Clinic, Mayo Foundation for Medical Education and Research, Feb. 15, 2024 (Year: 2024).*
Li et al. Genes Immun. Jul. 2008;9(5):395-404 (Year: 2008).*
Ren et al. Mediators Inflamm. 2016;2016:5147571 (Year: 2016).*
Pap et al. Kidney Blood Press Res. 2017;42(1):16-32. Epub Feb. 28, 2017. (Year: 2017).*
Kreuter et al. Dtsch Arztebl Int. Mar. 5, 2021:118:152-62. (Year: 2021).*
Narayana Health "Renal Fibrosis: Causes, Symptoms, and Treatment Options" Oct. 20, 2023. Accessed online Apr. 22, 2025. (Year: 2023).*
Li et al., Interleukin-20 induced cell death in renal epithelial cells and was associated with acute renal failure. Genes Immun. Jul. 2008;9(5):395-404. Epub May 22, 2008.
Li et al., Rapid pulmonary fibrosis induced by acute lung injury via a lipopolysaccharide three-hit regimen. Innate Immun. Jun. 2009;15(3):143-54.
Venkataraman et al., The role of epidermal growth factor receptor (EGFR) signaling in SARS coronavirus-induced pulmonary fibrosis. Antiviral Res. Jul. 2017;143:142-150. Epub Apr. 5, 2017.
Wan, Endostatin, an angiogenesis inhibitor, ameliorates bleomycin-induced pulmonary fibrosis in rats. Respir Res. May 20, 2013;14(1):56(1-13).
Xu et al., $PM_{2.5}$ induced pulmonary fibrosis in vivo and in vitro. Ecotoxicol Environ Saf. Apr. 30, 2019;171:112-121. Epub Dec. 28, 2018.
Zuo et al., SARS Coronavirus and Lung Fibrosis. Molecular Biology of the SARS-Coronavirus. Jul. 22, 2009:247-58.
Madouri et al. (2018) "Production of Interleukin-20 Cytokines Limits Bacterial Clearance and Lung Inflammation During Infection by *Streptococcus pneumoniae*", EBioMedicine, 37:417-427.

* cited by examiner

*Primary Examiner* — Jeffrey Stucker
*Assistant Examiner* — Sarah Cooper Patterson
(74) *Attorney, Agent, or Firm* — Mintz Levin Cohn Ferris Glovsky and Popeo, P.C.

(57) ABSTRACT

Methods of treating tissue fibrosis and/or injury and/or organ failure using an interleukin 24 (IL-24) protein or an interleukin 20 (IL-20) antagonist are provided.

11 Claims, 16 Drawing Sheets

Specification includes a Sequence Listing.

100
TREATING TISSUE FIBROSIS WITH INTERLEUKIN 24

CROSS REFERENCE TO RELATED APPLICATIONS

The present application is a United States National Phase under 35 U.S.C. § 371 of International Application No. PCT/US2020/057781, filed Oct. 28, 2020, which claims priority to U.S. Provisional Application No. 62/926,884, filed on Oct. 28, 2019, the contents of each of which are incorporated by reference in their entirety.

SEQUENCE LISTING

The application contains a Sequence Listing that has been filed electronically in the form of a text file, created Apr. 26, 2022, and named "114812-0026_Sequence-Listing.TXT" (20,468 bytes), the contents of which are incorporated by reference herein in their entirety.

FIELD OF THE INVENTION

The present disclosure relates to a field of treatment and/or prevention of tissue fibrosis and/or injury and/or organ failure. Particularly, the present disclosure denotes the use of IL-24 or its agonists and IL-20 antagonists (such as anti-IL-20 antibodies) to treat or prevent tissue fibrosis and/or injury and/or organ failure.

BACKGROUND OF THE INVENTION

Interleukin 24 (IL-24), also known as melanoma differentiation-associated 7 (mda-7), is a cytokine belonging to the IL-10 family. IL-24 is predominantly produced by immune cells such as activated monocytes, macrophages, and T cells. It has been reported that IL-24 may play roles in controlling cell survival and proliferation by inducing rapid activation of transcription factors STAT1 and STAT3.

Interleukin IL-20 (IL-20) is a member of the IL-10 family, which includes IL-10, IL-19, IL-20, IL-22, IL-24, and IL-26. Blumberg, et al., 2001, Cell 104:9-19; Pestka et al., 2004, Annu Rev Immunol 22:929-979. IL-20 is expressed in monocytes, epithelial cells, and endothelial cells and acts on multiple cell types by activating a heterodimer receptor complex of either IL-20R1/IL-20R2 or IL-22R1/IL-20R2. Dumoutier, et al., 2001, J Immunol 167:3545-3549). IL-20 was found to be involved in various inflammatory diseases, such as psoriasis (Blumberg et al., 2001; Sa et al., 2007, J Immunol 178:2229-2240; and Wei et al., 2005, Clin Immunol 117:65-72), rheumatoid arthritis (Hsu, et al., 2006, Arthritis Rheum 54:2722-2733), atherosclerosis (Caligiuri, et al. 2006, Arterioscler Thromb Vasc Biol 26:1929-1930; and Chen et al., 2006, Arterioscler Thromb Vasc Biol 26:2090-2095), ischemic stroke (Chen et al., 2009, J Immunol 182:5003-5012), and renal failure (Li et al., 2008, Genes Immun 9:395-404). See also Wei et al., 2006, J Biomed Sci 13:601-612.

There remains a need to increase the efficacy of organ disease treatments.

SUMMARY OF THE INVENTION

The present disclosure is based on the surprising and unexpected results that IL-24 or an IL-20 antagonist successfully reduced symptoms of tissue fibrosis and/or injury and/or organ failure such as renal fibrosis and pulmonary fibrosis and prolonged survival rate of mice suffering from renal and pulmonary injury.

Accordingly, one aspect of the present disclosure features a method for alleviating or delaying the onset of or treating a tissue fibrosis and/or injury and/or organ failure occurred in kidney or lung, comprising administering an effective amount of an interleukin 24 (IL-24) protein or an interleukin 20 (IL-20) antagonist to a subject in need of alleviating or delaying the onset of or treating a tissue fibrosis and/or injury and/or organ failure occurred in lung, or administering an effective amount of an interleukin 24 (IL-24) to a subject in need of alleviating or delaying the onset of or treating a tissue fibrosis and/or injury and/or organ failure occurred in kidney.

In some embodiments, the subject is a human patient having or suspected of having the tissue fibrosis and/or injury and/or organ failure. In some embodiments, the tissue fibrosis and/or injury and/or organ failure occurred in kidney is selected from the group consisting of renal fibrosis, chronic kidney disease, chemotherapy-induced renal fibrosis (for example, doxorubicin-induced renal fibrosis) and diabetes-induced nephropathy. In some embodiments, the tissue fibrosis and/or injury and/or organ failure occurred in lung is selected from the group consisting of pulmonary fibrosis, pulmonary inflammation, idiopathic pulmonary fibrosis, air pollution-induced pulmonary fibrosis (for example, $PM_{2.5}$-induced pulmonary fibrosis), chemotherapy-induced pulmonary fibrosis (for example, bleomycin-induced pulmonary fibrosis), antibiotic-induced pulmonary fibrosis (for example, glycol-peptide antibiotic-induced pulmonary fibrosis) and infection-induced pulmonary fibrosis (for example, SARS-CoV-2 infection-induced pulmonary fibrosis).

In any of the methods described herein, the pharmaceutical composition can be administered by a systemic route. In some examples, the pharmaceutical composition is administered parenterally. For example, the pharmaceutical composition can be administered via intravenous infusion or intraperitoneal injection.

Any of the methods described herein, the pharmaceutical composition comprising the IL-24 protein and the interleukin 20 antagonist.

The IL-20 antagonist may be an antibody binding to human IL-20 or an antibody binding to a human IL-20 receptor, e.g., those described herein. In some embodiments, the IL-20 antagonist can be an antibody that binds to IL-20 or an IL-20 receptor, thereby inhibiting a signaling pathway mediated by IL-20. For example, such an antibody may bind to an IL-20 protein (e.g., human IL-20) or may bind to an IL-20 receptor (e.g., a human IL-20 receptor such as R1 subunit of an IL-20). Any of the exemplary antibodies used in the method described herein can be a full-length antibody or an antigen-binding fragment thereof. Alternatively, the antibody can be a human antibody, a humanized antibody, a chimeric antibody, or a single-chain antibody.

In one aspect, an exemplary antibody that binds human IL-20 used herein can be a monoclonal antibody mAb7E, an antigen-binding fragment thereof, or a functional variant thereof. In one example, a functional variant of mAb7E comprises the same complementary determining regions (CDRs) as mAb7E. In another example, the functional variant is a humanized antibody of mAb7E. Such a humanized antibody can comprises a heavy chain variable region ($V_H$), which comprises the amino acid sequence of SEQ ID NO: 8, and a light chain variable region (V$_L$), which comprises the amino acid sequence of SEQ ID NO: 12 or SEQ ID NO: 13.

In some embodiments, the IL-20 antagonist is an antibody binding to human IL-20 or an antibody binding to a human IL-20 receptor, and the IL-24 protein and the antibody are conjugated as one single molecule.

Also within the scope of the present disclosure are pharmaceutical compositions comprising any of the IL-24 proteins or IL-20 antagonist disclosed herein for use in treating tissue fibrosis and/or injury and/or organ failure, and uses of any of the IL-24 or IL-20 antagonist proteins in manufacturing a medicament for use in treating tissue fibrosis and/or injury and/or organ failure.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1. IL-24 expression was down-regulated in fibrotic area of renal tissues with CKD. Immunofluorescence staining of IL-24 in renal sections of patients with CKD was shown. Induction of progressive renal fibrosis animal model and the accumulation of collagen in the renal tissue with UUO surgery.

FIG. 2. IL-24 protein-treatment prevent against renal fibrosis in long-term UUO mice. UUO mice were induced for 4 weeks to establish long-term renal fibrosis. Treatment with mouse recombinant IL-24 protein (IL-24) was started after 24 hours of UUO surgery. (n=4 each group).

FIG. 3. IL-24 mice were protected against UUO-induced renal fibrosis. UUO mice were induced for 2 weeks. Mice were injected with IL-24 protein after 2 weeks of UUO surgery. (n=5 each group).

FIG. 4. IL-24 treatment alleviated doxorubicin-induced nephrotoxicity. Mice were induced by Doxorubicin (Dox) (5 mg/kg/week) for 4 consecutive weeks to establish nephrotoxicity model. Treatment with mouse recombinant IL-24 protein (1 mg/kg), twice/week, was started 2 weeks after Dox-induction on mice and euthanized on Day 42 (n=5 each group).

DETAILED DESCRIPTION OF THE INVENTION

Figure 1A:
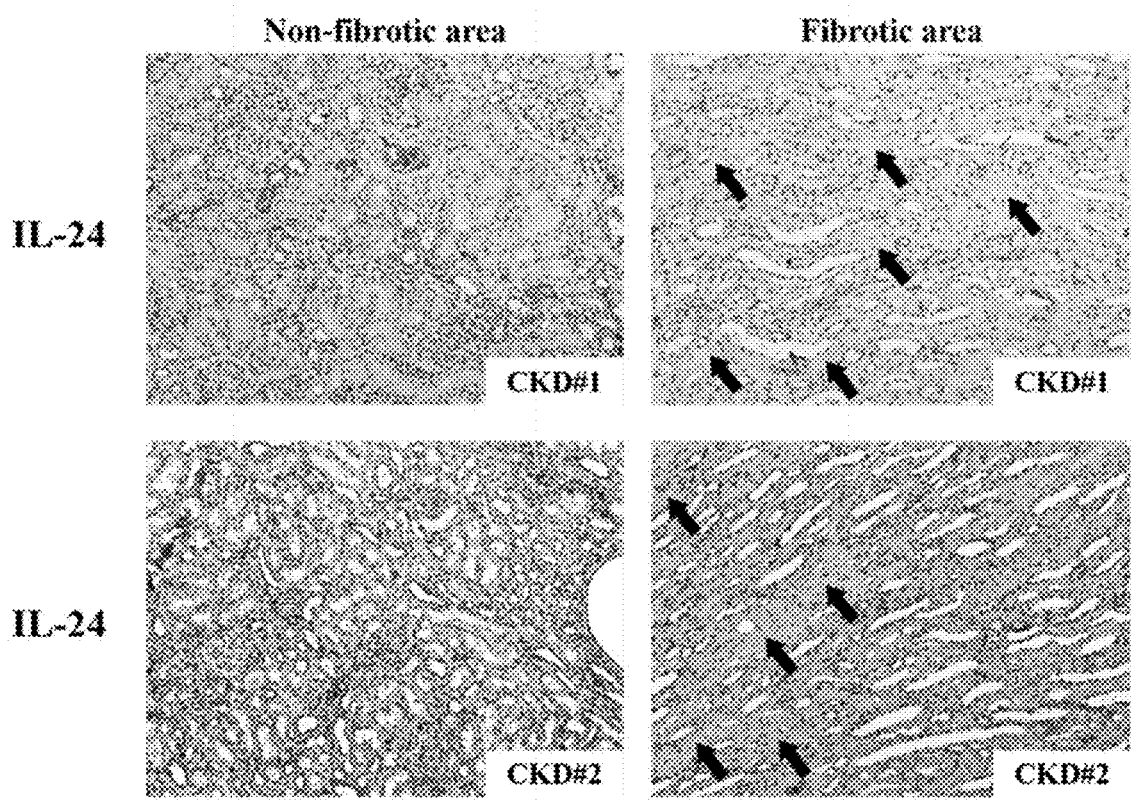
FIG. 1A: Immunohistochemistry was used to detect the expression level of hIL-24. Nuclei were stained with hematoxylin. Original magnification: 200×.

The present disclosure is based on the unexpected results that interleukin 24 (IL-24) or an interleukin 20 (IL-20) antagonist showed protective effects in a well-recognized mouse model for human tissue fibrosis and/or injury and/or organ failure. Specifically, IL-24 was found to protect mice from renal fibrosis in chronic kidney disease and long-term unilateral ureteral obstruction, decrease serum creatinine and BUN, decrease the expression of pro-fibrogenic factors, reduce collagen production, maintain renal function, inhibit and reverse TGF-β-induced epithelial-mesenchymal transition, resist to Doxorubicin-induced renal injury in mice. Specifically, IL-24 or the interleukin 20 antagonist was found to ameliorate pulmonary fibrosis and cause the decrease of TGFβ, αSMA expression, and collagen deposition in lung tissue. Accordingly, provided herein are methods of alleviating and/or delaying the onset of tissue fibrosis and/or injury and/or organ failure with an effective amount of an IL-24 protein or the interleukin 20 antagonist.

I. IL-24 Proteins

IL-24 is a member of the IL-10 cytokine superfamily. The structural and functional information of this cytokine were well known in the art. IL-24 binds two heterodimeric receptors, IL-20R1/IL-20R2 and IL-22R1/IL-20R2 and activates rapidly transcription factors Stat-1 and Stat-3, which play essential roles in cell survival and proliferation. Wang et al., *Immunology*, 114:166-170 (2005). IL-24 proteins are highly homologous across species. The human IL-24 shares close to 70% sequence identity to mouse and rat IL-24, indicating that this cytokine may function across species. Rodent IL-24 proteins were found to be able to activate human IL-24 receptors. Wang et al., *Genes Immun* 5:363-370 (2004).

Mature human IL-24 is a glycoprotein having a molecular weight of around 33,000 kDal. The amino acid sequence of an exemplary human IL-24 can be found under GenBank accession no. AAH09681.1. Mature rat and mouse IL-24 have a molecular weight of around 23,000 kDal. Amino acid sequences of exemplary rat and mouse IL-24 can be found under GenBank accession no. NP_579845.1 and NP_444325.2.

The IL-24 proteins described herein refer to polypeptides having the same bioactivity as a naturally-occurring IL-24, for example, the human IL-24. In some embodiments, the IL-24 proteins used in the method described herein is a native IL-24 protein obtained from a suitable species, e.g., human, a non-human primate such as monkey, rat, mouse, pig, bovine, rabbit, etc. Such native IL-24 proteins include naturally-occurring isoforms such as polymorphism variants and slice variants.

In some examples, the IL-24 protein is a human protein. Examples include the IL-24 protein described in GenBank accession no. AAH09681.1, human IL-24 isoform 1 described in GenBank accession no. NP_006841.1, human IL-24 isoform 3 described in GenBank accession no. NP_001172085.1, human IL-24 isoform 4 described in GenBank accession no. NP_001172086.1, human IL-24 isoform 5 described in GenBank accession no. NP_001172087.1, human IL-24 splice variant delE3 described in GenBank accession no. AAV52800.1, and human IL-24 splice variant delE5 described in GenBank accession no. AAV52801.1.

In other examples, the IL-24 protein is a native IL-24 protein derived from a suitable mammal such as a non-human primate, rat, mouse, pig, bovine, rabbit, etc. Examples include gorilla IL-24 (e.g., that disclosed under GenBank accession no. XP_004028343), a chimpanzee IL-24 (e.g., that disclosed under GenBank accession no. XP_008974768.1), orangutan IL-24 (e.g., those disclosed under GenBank accession nos. XP_002809582.1 and XP_009236749.1), a bovine IL-24 (such as that described under GenBank accession nos. XP_010363962), and a rodent IL-24 such as the rat and mouse IL-24 proteins described above.

The IL-24 protein described herein may be a native IL-24 protein that shares at least about 65% (e.g., about 70%, 75%, 80%, 85%, 90%, 95%, 98%, or above) sequence identity to a human counterpart as those described herein. The term "about" allows for an up to 5% variation from the reference value. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the)(BLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Alternatively, the IL-24 protein can be a functional variant of a naturally-occurring IL-24 protein. A functional variant of a naturally-occurring IL-24 can share a high sequence homology with the native counterpart (e.g., at least about 80%, 85%, 90%, 95%, 98% or above) and contain one or more mutations relative to the native counterpart. Typically, such mutations should occur at regions that do not substantially affect the bioactivity of the IL-24 protein. Structural features of IL-24, as a member of the IL-19 subfamily, were well known in the art. Zdanov, Vitam Horm, 74:61-76 (2006). Functional domains of IL-24 can also be identified by comparing the amino acid sequence of a particular IL-24 protein with other members of the IL-24 family and/or the IL-10/IL-19 family. In some instances, the functional variant contains up to 10 (e.g., 9, 8, 7, 6, 5, 4, 3, 2, or 1) amino acid substitutions as compared with the native counterpart. The activity of a candidate functional variant can be verified by routine methodology.

The skilled artisan will realize that conservative amino acid substitutions may be made to a wild-type IL-24 to provide functional variants, i.e., the variants retain the functional capabilities of the particular IL-24 protein. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of a native IL-24 to produce functional variants typically are made by alteration of a nucleic acid encoding the native IL-24. Such substitutions can be made by a variety of methods known to one of ordinary skill in the art. For example, amino acid substitutions may be made by PCR-directed mutation, site-directed mutagenesis according to the method of Kunkel (Kunkel, PNAS 82: 488-492, 1985), or by chemical synthesis of a nucleic acid molecule encoding an IL-24 protein.

Any of the IL-24 proteins described herein can be prepared by routine technology, for example, recombinant technology. Native IL-24 proteins can also be isolated from a suitable natural source.

II. IL-20 Antagonists

Exemplary IL-20 can include a pro-inflammatory cytokine that belongs to the IL-10 cytokine family. The IL-20 described herein refers to interleukin-20 and variants thereof that retain at least part of the activity of IL-20. As used herein, IL-20 includes all mammalian species of native sequence IL-20, including human, canine, feline, equine, or bovine. In one example, the IL-20 is a human IL-20 (GenBank accession no. NP_061194.2).

IL-20 activates the IL-20 signaling pathway via binding to IL-20 receptor, which is a dimeric complex contains subunits IL-20R1 and IL-20R2 (also known as RA and RB). Such an IL-20 receptor is shared by three functionally different cytokines, i.e., IL-19, IL-20, and IL-24, suggesting that this receptor mediates different signaling pathways dependent upon its binding to a specific cytokine. IL-20 is also capable of binding to a dimeric complex containing IL-20R2 and IL-22R1. The IL-20 receptor disclosed herein refers to one or more polypeptides that are capable of binding to and being activated by IL-20. IL-20 receptors disclosed herein include IL-20R1, IL-20R2 and IL-22R1 of any mammalian species, including, but are not limited to, human, canine, feline, equine, primate, or bovine. Examples of human IL-20 receptors include hIL-20R1 (GenBank Accession No. NM 014432.2), hIL-20R2 (GenBank Accession No. NM_144717.2) and hIL-22R1 (NM_181309.1). Sequences of human IL-20 receptors have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1.

The IL-20 antagonist to be used in the methods described herein is a molecule that blocks, suppresses, or reduces (including significantly) the biological activity of IL-20, including downstream pathways mediated by IL-20 signaling, such as receptor binding and/or elicitation of a cellular response to IL-20. See US2011/0064731, which is incorporated by reference herein in its entirety. The term "antagonist" implies no specific mechanism of biological action whatsoever, and is deemed to expressly include and encompass all possible pharmacological, physiological, and biochemical interactions with IL-20 whether direct or indirect. For purpose of the present disclosure, it will be explicitly understood that the term "antagonist" encompass all the previously identified terms, titles, and functional states and characteristics whereby the IL-20 itself (e.g., human IL-20), an IL-20 biological activity (including but not limited to its ability to mediate any aspect of pancreatic cancer), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

Exemplary IL-20 antagonists include, but are not limited to, an anti-IL-20 antibody, an anti-sense nucleic acid molecule directed to an IL-20 (including an anti-sense nucleic acid directed to a nucleic acid encoding IL-20), a small interfering RNA (siRNA) directed toward an IL-20 nucleic acid, a microRNA directed toward an IL-20 nucleic acid, an IL-20 inhibitory compound, an anti-IL-20R antibody (e.g., an antibody specifically binds IL-20R1, IL-20R2, or the dimeric complex formed thereby), an antisense nucleic acid molecule directed to a subunit of an IL-20 receptor, an siRNA or a microRNA directed to a nucleic acid encoding a subunit of an IL-20 receptor, or an IL-20R inhibitory compound. In some embodiments, an IL-20 antagonist binds IL-20 or IL-20 receptor and prevents the formation of IL-20-IL-20R complex, thereby inhibiting the IL-20 signaling pathway. In other embodiments, an IL-20 antagonist inhibits or reduces IL-20 synthesis and/or production (release). Such antagonists include antisense molecules, siRNAs and microRNAs.

Antibodies Capable of Interfering with the IL-20 Signaling Pathway

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one embodiment, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another embodiment, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In other embodiments, the antibody disclosed herein specifically binds a target antigen, such as human IL-20 or one of the two subunits of a human IL-20 receptor (e.g., IL-20R1). An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an IL-20 epitope is an antibody that binds this IL-20 epitope with greater affinity, avidity, more readily, and/or with greater duration than it binds to other IL-20 epitopes or non-IL-20 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of interfering with the IL-20 signaling pathway can be an antibody that binds an IL-20 (e.g., a human IL-20) and inhibits IL-20 biological activity and/or downstream pathways mediated by IL-20. Alternatively, such antibodies can be antibodies that bind an IL-20 receptor (IL-20R), e.g., bind to one or both of the subunits of the IL-20 receptor, and suppress the downstream signaling pathways mediated by the receptor triggered by IL-20.

(i) Anti-IL-20 Antibodies

An anti-IL-20 antibody is an antibody capable of binding to IL-20 and inhibits IL-20 biological activity and/or downstream pathway(s) mediated by IL-20 signaling. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000.

The binding affinity of an anti-IL-20 antibody to IL-20 (such as human IL-20) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to IL-20 is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25 .degree. C.) are obtained; and equilibrium dissociation constant ($K_D$) values are calculated as $k_{off}/k_{on}$.

In some embodiments, the antibody binds human IL-20, and does not significantly bind an IL-20 from another mammalian species. In some embodiments, the antibody binds human IL-20 as well as one or more IL-20 from another mammalian species. In still other embodiments, the antibody binds IL-20 and does not significantly cross-react with other cytokines (such as the related cytokines IL-10, IL-17A, IL-19, IL-22, IL-24 and IL-26). The epitope(s) bound by the antibody can be continuous or discontinuous.

In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. See also U.S. Pat. Nos. 8,206,712 and 7,611,705, the relevant disclosures of each of which are incorporated by reference herein.

The amino acid sequences and encoding nucleotide sequences of the heavy chain variable region ($V_H$) and light chain variable region ($V_L$) of mAb7E are produced below.

```
Nucleotide sequence (SEQ ID NO: 1) and amino acid
sequence (SEQ ID NO: 2) of mAb 7E heavy chain variable
region
gaa ttg aag ctt gag gag tct gga gga ggc ttg gtg cag cct gga   45
 E   L   K   L   E   E   S   G   G   G   L   V   Q   P   G    15 gga tcc atg aaa ctc tct tgt gct gcc tct gga ttc act ttt agt   90
 G   S   M   K   L   S   C   A   A   S   G   F   T   F   S    30
```

-continued

```
gac gcc tgg atg gac tgg gtc cgc cag tct cca gag aag ggg ctt  135
 D   A   W   M   D   W   V   R   Q   S   P   E   K   G   L    45 gag tgg att gct gaa att aga agc aaa gct aat aat tat gca aca  180
 E   W   I   A   E   I   R   S   K   A   N   N   Y   A   T    60 tac ttt gct gag tct gtg aaa ggg agg ttc acc atc tca aga gat  215
 Y   F   A   E   S   V   K   G   R   F   T   I   S   R   D    75 gat tcc aaa agt ggt gtc tac ctg caa atg aac aac tta aga gct  270
 D   S   K   S   G   V   Y   L   Q   M   N   N   L   R   A    90 gag gac act ggc att tat ttc tgt acc aag tta tca cta cgt tac  315
 E   D   T   G   I   Y   F   C   T   K   L   S   L   R   Y   105 tgg ttc ttc gat gtc tgg ggc gca ggg acc acg gtc acc gtc tcc  360
 W   F   F   D   V   W   G   A   G   T   T   V   T   V   S   120 tca                                                          363
 S                                                           121

Nucleotide sequence (SEQ ID NO: 3) and amino acid
sequence (SEQ ID NO: 4) of mAb 7E light chain variable
region
gat ttt gtg atg acc cag act cca ctc act ttg tcg gtt acc att   45
 D   F   V   M   T   Q   T   P   L   T   L   S   V   T   I    15 gga caa cca gcc tcc atc tct tgc aag tca agt cag agc ctc ttg   90
 G   Q   P   A   S   I   S   C   K   S   S   Q   S   L   L    30 gat agt gat gga aag aca tat ttg aat tgg ttg tta cag agg cca  135
 D   S   D   G   K   T   Y   L   N   W   L   L   Q   R   P    45 ggc cag tct cca aag cac ctc atc tat ctg gtg tct aaa ctg gac  180
 G   Q   S   P   K   H   L   I   Y   L   V   S   K   L   D    60 tct gga gtc cct gac agg ttc act ggc agt gga tca ggg acc gat  215
 S   G   V   P   D   R   F   T   G   S   G   S   G   T   D    75 ttc aca ctg aga atc agc aga gtg gag gct gag gat ttg gga gtt  270
 F   T   L   R   I   S   R   V   E   A   E   D   L   G   V    90 tat tat tgc tgg caa agt aca cat ttt ccg tgg acg ttc ggt gga  315
 Y   Y   C   W   Q   S   T   H   F   P   W   T   F   G   G   105 ggc acc aag ctg gaa atc aaa cgg                              339
 G   T   K   L   E   I   K   R                               113
```

A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs.

In addition, determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

In some examples, a functional variant of mAb7E comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7E, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7E.

Alternatively, the functional variant of mAb7E comprises a $V_H$ chain at least 75% (e.g., 80%, 85%, 90%, 95%, or 98%) identical to the $V_H$ chain (mature or precursor) of mAb7E and a $V_L$ chain at least 75% (e.g., 80%, 85%, 90%, 95%, or 98%) identical to the $V_L$ chain (mature of precursor) of mAb7E.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other examples, a functional variant of mAb7E comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7E, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7E.

Functional variants of mAb7E are also disclosed in U.S. Pat. No. 7,611,705 and US2011/0064731, both of which are incorporated by reference herein.

In one example, a functional variant of mAb7E is a humanized antibody derived from mAb7E. Provided below are exemplary humanized mAb7E antibodies HL1 and HL2; see also U.S. Pat. No. 8,597,647, the relevant disclosures therein are incorporated by reference.

Amino acid sequence and encoding nucleotide sequence of the $V_H$ chain of humanized anti-IL-20 antibodies HL1 and HL2:

```
                                                              (SEQ ID NO: 5)
ATG TAC TTG GGA CTG AAC TAT GTT
                                                              (SEQ ID NO: 6)
 M   Y   L   G   L   N   Y   V

TTC ATC GTT TTT CTC CTG AAT GGT GTC CAG AGT GAA
 F   I   V   F   L   L   N   G   V   Q   S   E

GTG CAG CTT GTG GAG TCT GGA GGA GGC TTG GTG CAG
 V   Q   L   V   E   S   G   G   G   L   V   Q

CCT GGA GGA TCC CTG AAA CTC TCT TGT GCT GCC TCT
 P   G   G   S   L   K   L   S   C   A   A   S

GGA TTC ACT TTT AGT GAC GCC TGG ATG GAC TGG GTC
 G   F   T   F   S   D   A   W   M   D   W   V

CGC CAG GCT TCC GGG AAG GGG CTT GAG TGG ATT GCT
 R   Q   A   S   G   K   G   L   E   W   I   A

GAA ATT AGA AGC AAA GCT AAT AAT TAT GCA ACA TAC
 E   I   R   S   K   A   N   N   Y   A   T   Y

TTT GCT GAG TCT GTG AAA GGG AGG TTC ACC ATC TCA
 F   A   E   S   V   K   G   R   F   T   I   S

AGA GAT GAT TCC AAA AAC ACC GCC TAC CTG CAA ATG
 R   D   D   S   K   N   T   A   Y   L   Q   M

AAC AGC TTA AAA ACC GAG GAC ACT GCC GTT TAT TAC
 N   S   L   K   T   E   D   T   A   V   Y   Y

TGT ACC AAG TTA TCA CTG CGT TAC TGG TTC TTC GAT
 C   T   K   L   S   L   R   Y   W   F   F   D

GTC TGG GGC CAG GGG ACC CTG GTC ACC GTC TCC TCA
 V   W   G   Q   G   T   L   V   T   V   S   S
```

The underlined region refers to the signal peptide and the boldfaced/italic regions are the CDRs. SEQ ID NOs: 8 and 7 represent the mature $V_H$ amino acid sequence (lacking the signal peptide) and its encoding nucleotide sequence, respectively.

Amino acid sequence and encoding nucleotide sequence of the $V_L$ chain (VL2) of a humanized anti-IL-20 antibody HL2:

```
                                                              (SEQ ID NO: 9)
ATG ATG AGT CCT GCC CAG TTC CTG TTT
                                                              (SEQ ID NO: 10)
 M   M   S   P   A   Q   F   L   F

CTG TTG GTG CTC TGG ATT CGG GAA ACC AAC GGT GAT
 L   L   V   L   W   I   R   E   T   N   G   D

ATC GTG ATG ACC CAG ACT CCA CTC TCT TTG TCC GTT
 I   V   M   T   Q   T   P   L   S   L   S   V

ACC CCT GGA CAA CCA GCC TCC ATC TCT TGC AAG TCA
 T   P   G   Q   P   A   S   I   S   C   K   S

AGT CAG AGC CTC TTG GAT AGT GAT GGA AAG ACA TAT
 S   Q   S   L   L   D   S   D   G   K   T   Y

TTG AAT TGG TTG TTA CAG AAG CCA GGC CAG TCT CCA
 L   N   W   L   L   Q   K   P   G   Q   S   P
```

-continued

```
CAG CAC CTC ATC TAT CTG GTG TCT AAA CTG GAC TCT
 Q   H   L   I   Y   L   V   S   K   L   D   S

GGA GTC CCT GAC AGG TTC AGT GGC AGT GGA TCA GGG
 G   V   P   D   R   F   S   G   S   G   S   G

ACC GAT TTC ACA CTG AAA ATC AGC AGA GTG GAG GCT
 T   D   F   T   L   K   I   S   R   V   E   A

GAG GAT GTT GGA GTT TAT TAT TGC TGG CAA AGT ACA
 E   D   V   G   V   Y   Y   C   W   Q   S   T

CAT TTT CCC TGG ACC TTC GGT GGA GGC ACC AAG GTG
 H   F   P   W   T   F   G   G   G   T   K   V

GAA ATC AAA
 E   I   K
```

The underlined region refers to the signal peptide and the boldfaced/italic regions are the CDRs. SEQ ID NOs: 12 and 11 represent the mature $V_L$ amino acid sequence (lacking the signal peptide) and its encoding nucleotide sequence, respectively.

Humanized antibody HL1 comprises the same $V_H$ chain as HL2 and a $V_L$ chain (SEQ ID NO: 13; mature form) that is otherwise identical to the $V_L$ of HL2 except that the I residue at position 2 of mature $V_L$ of HL2 is replaced with F.

Also disclosed herein are functional variants of the above-noted humanized antibodies HL1 and HL2. Such functional variants can comprise a $V_H$ chain that comprises an amino acid sequence at least 85% (e.g., 90%, 92%, 94%, 95%, 96%, 97%, 98%, or 99%) identical to that of the $V_H$ of HL1 and HL2 (precursor or mature form; SEQ ID NO: 6 and SEQ ID NO: 8, respectively) and a $V_L$ chain that has an amino acid sequence at least 85% (e.g., 90%, 92%, 94%, 95%, 96%, 97%, 98%, or 99%) identical to that of the $V_L$ of HL2 (precursor or mature form; SEQ ID NO: 10 and SEQ ID NO: 12, respectively). These variants are capable of binding to an IL-20 molecule, particularly a human IL-20 molecule. In some examples, the variants possess similar antigen-binding affinity relative to the exemplary humanized antibody described above (e.g., having a $K_d < 4^{10}$)

(ii) Antibody Preparation

Antibodies capable of interfering with the IL-20 signaling pathway as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human IL-20 or IL-20R1) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-IL-20 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the IL-20 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by IL-20. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the IL-20 polypeptide have been replaced (swapped) with sequences from a closely related, but antigenically distinct protein (such as another member of the neurotrophin protein family). By assessing binding of the antibody to the mutant IL-20, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

(iii) Other IL-20 Antagonists

IL-20 antagonists other than antibodies capable of interfering with the IL-20 signaling pathway as described above can be used in the methods described herein.

In some embodiments of the invention, the IL-20 antagonist comprises at least one antisense nucleic acid molecule capable of blocking or decreasing the expression of a functional IL-20 (e.g., a human IL-20) or a subunit of an IL-20 receptor (e.g., IL-20R1). Nucleotide sequences of the IL-20 and IL-20 receptor subunits are known and are readily available from publicly available databases. See above disclosures. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

Alternatively, IL-20/IL-20R expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the IL-20 antagonist comprises at least one IL-20 or IL-20R inhibitory compound. As used herein, "IL-20 inhibitory compound" or "IL-20R inhibitory compound" refers to a compound other than an anti-IL-20 or anti-IL-20R antibody that directly or indirectly reduces, inhibits, neutralizes, or abolishes IL-20/IL-20R biological activity. An IL-20/IL-20R inhibitory compound should exhibit any one or more of the following characteristics: (a) binds to IL-20 or IL-20R and inhibits its biological activity and/or downstream pathways mediated by IL-20 signaling function; (b) prevents, ameliorates, or treats any aspect of eye disease; (c) blocks or decreases IL-20 receptor activation; (d) increases clearance of IL-20 or IL-20R; (e) inhibits (reduces) IL-20 or IL-20R synthesis, production or release. One skilled in the art can prepare other small molecules inhibitory compounds.

In some embodiments, an IL-20 or IL-20R inhibitory compound is an IL-20 mutant, an IL-19 mutant, or an IL-24 mutant, which can bind to an IL-20 receptor but cannot elicit signal transduction. Such a mutant may block binding of wild type IL-20 to an IL-20 receptor thus preventing IL-20 signal transduction.

In other embodiments, the IL-20 or IL-20R inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the IL-20-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In other embodiments, the IL-20 antagonists can be a polypeptide comprising an extracellular portion of an IL-20 receptor (such as IL-20 R1, IL-20R2, or IL-22R1), wherein the polypeptide specifically binds to Il-20 and blocks its interaction with one or more IL-20 receptors. In some embodiments, the extracellular portion of the IL-20 receptor is fused to a Fc domain of antibody. Examples of the soluble receptors are described in PCT WO 01/46232.

(iv) Identification of IL-20 Antagonists

IL-20 antagonists can be identified or characterized using methods known in the art, whereby reduction, amelioration, or neutralization of an IL-20 biological activity is detected and/or measured. For example, an ELISA-type assay may be suitable for qualitative or quantitative measurement of IL-20 mediated kinase activation by measuring the phosphorylation of proteins activated through an IL-20 cascade. Examples include JNK, ERK, AKT, p38, STAT3 and TRAF6.

The IL-20 antagonists can also be identified by incubating a candidate agent with IL-20 or IL-20R and monitoring any one or more of the following characteristics: (a) binding to IL-20 or IL-20R and inhibiting its biological activity and/or downstream pathways mediated by IL-20 signaling function; (b) preventing, ameliorating, or treating any aspect of eye disease; (c) blocking or decreasing IL-20 receptor activation; (d) increasing clearance of IL-20 or IL-20R; (e) inhibiting (reducing) IL-20 synthesis, production or release. In some embodiments, an IL-20 antagonist is identified by incubating a candidate agent with IL-20 or IL-20R and monitoring binding and attendant reduction or neutralization of a biological activity of IL-20 or IL-20R. The binding assay may be performed with purified IL-20 or IL-20R polypeptide(s), or with cells naturally expressing, or transfected to express, IL-20 or IL-20R polypeptide(s). In one embodiment, the binding assay is a competitive binding assay, where the ability of a candidate antibody to compete with a known IL-20 antagonist for IL-20 or IL-20R binding is evaluated. The assay may be performed in various formats, including the ELISA format. In other embodiments, an IL-20 antagonist is identified by incubating a candidate agent with IL-20 or IL-20R (e.g., IL-20R1) and monitoring attendant inhibition of IL-20R1/IL-20R2 complex formation or IL-20R2/IL-22R1 complex formation. Following initial identification, the activity of a candidate IL-20 antagonist can be further confirmed and refined by bioassays, known to test the targeted biological activities. Alternatively, bioassays can be used to screen candidates directly.

The examples provided below provide a number of assays that can be used to screen candidate IL-20 antagonists. Bioassays include but are not limited to flow cytometry of determine competitive binding of IL-20 to cells in the presence of candidate IL-20 antagonists; and inhibition of IL-20-induced apoptosis in renal epithelial cells. In addition, RT-PCR or Real-time PCR which can be used to directly measure IL-20 expression or to measure expression of genes upregulated by IL-20 such as TNFα MCP-1, IL-1β, IL-6 and VEGF.

II. Pharmaceutical Compositions

An IL-24 protein or the interleukin 20 antagonist as described herein can be mixed with a pharmaceutically acceptable carrier (excipient), including buffer, to form a pharmaceutical composition for use in alleviating a tissue fibrosis and/or injury and/or organ failure. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the IL-24 protein, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., an IL-24 protein or the interleukin 20 antagonist) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the IL-24 protein, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(—)-3-hydroxybutyric acid.

The pharmaceutical compositions to be used for in vivo administration must be sterile. This is readily accomplished by, for example, filtration through sterile filtration membranes. Therapeutic IL-24 or the interleukin 20 antagonist-containing compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™, and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an IL-24 protein with Intralipid™ or the components thereof (soybean oil, egg phospholipids, glycerol and water, etc.).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

III. Treating Tissue Fibrosis and/or Injury and/or Organ Failure

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerobrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, an IL-24 protein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having the tissue fibrosis and/or injury and/or organ failure, including renal fibrosis, chronic kidney disease, chemotherapy-induced renal fibrosis, diabetes-induced nephropathy, pulmonary fibrosis, pulmonary inflammation, idiopathic pulmonary fibrosis, air pollution-induced pulmonary fibrosis, chemotherapy-induced pulmonary fibrosis, antibiotic-induced pulmonary fibrosis, and infection-induced pulmonary fibrosis. A subject having the tissue fibrosis and/or injury and/or organ failure, e.g., those described herein, can be identified by routine medical examination, e.g., laboratory tests, organ functions tests, organ biopsy, CT scans, or ultrasounds. A subject suspected of having the tissue fibrosis and/or injury and/or organ failure occurred in kidney such as kidney fibrosis might show one or more symptoms of the disorder, e.g., increasing serum creatinine and BUN, decreasing the expression of pro-fibrogenic factors, reducing collagen production, maintaining renal function, inhibiting and reversing TGF-β-induced epithelial-mesenchymal transition, resisting to Doxorubicin-induced renal injury in mice. A subject suspected of having the tissue fibrosis and/or injury and/or organ failure occurred in lung such as pulmonary fibrosis might show one or more symptoms of the disorder, e.g., decreasing TGFβ, αSMA expression, and collagen deposition in lung tissue.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, human-based IL-24 proteins or the interleukin 20 antagonist may be used to prolong half-life of the cytokine and to prevent the cytokine being attacked by the host's immune system. Frequency of administration may be determined and adjusted over the course of therapy, and is generally, but not necessarily, based on treatment and/or suppression and/or amelioration and/or delay of the tissue fibrosis and/or injury and/or organ failure. Alternatively, sustained continuous release formulations of an IL-24 protein or the interleukin 20 antagonist may be appropriate. Various formulations and devices for achieving sustained release are known in the art.

In one example, dosages for an IL-24 protein or the interleukin 20 antagonist as described herein may be determined empirically in individuals who have been given one or more administration(s) of the IL-24 protein or the interleukin 20 antagonist. Individuals are given incremental dosages of the cytokine. To assess efficacy of the cytokine, an indicator of the tissue fibrosis and/or injury and/or organ failure occurred in kidney such as kidney fibrosis (e.g., levels of serum creatinine and BUN) can be followed. To assess efficacy of the cytokine, an indicator of the tissue fibrosis and/or injury and/or organ failure occurred in lung such as pulmonary fibrosis (e.g., levels of TGFβ, and αSMA) can be followed.

Generally, for administration of any of the IL-24 protein or the interleukin 20 antagonist described herein, an initial candidate dosage can be about 0.5-2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate tissue fibrosis and/or injury and/or organ failure, or a symptom thereof. An exemplary dosing regimen comprises administering an initial dose of about 2 mg/kg, followed by a weekly maintenance dose of about 1 mg/kg of the IL-24 protein or the interleukin 20 antagonist, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the IL-24 protein or the interleukin 20 antagonist used) can vary over time. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an IL-24 protein or the interleukin 20 antagonist will depend on the specific IL-24 protein or the interleukin 20 antagonist employed, the type and severity of tissue fibrosis and/or injury and/or organ failure, whether the IL-24 or the interleukin 20 antagonist is administered for preventive or therapeutic purposes, previous therapy, the patient's clinical history and response to the antagonist, and the discretion of the attending physician. Typically the clinician will administer an IL-24 protein, such as a human IL-24 protein, or the interleukin 20 antagonist, until a dosage is reached that achieves the desired result. Administration of an IL-24 protein or the interleukin 20 antagonist can be continuous or intermittent, depending, for example, upon the recipient's physiological condition, whether the purpose of the administration is therapeutic or prophylactic, and other factors known to skilled practitioners. The administration of an IL-24 protein or the interleukin 20 antagonist may be essentially continuous over a preselected period of time or may be in a series of spaced dose, e.g., either before, during, or after developing the tissue fibrosis and/or injury and/or organ failure.

As used herein, the term "treating" refers to the application or administration of a composition including one or more active agents to a subject, who has the tissue fibrosis and/or injury and/or organ failure occurred in kidney such as kidney fibrosis or the tissue fibrosis and/or injury and/or organ failure occurred in lung such as pulmonary fibrosis, a symptom of the disease, or a predisposition toward the disease, with the purpose to cure, heal, alleviate, relieve, alter, remedy, ameliorate, improve, or affect the disorder, the symptom of the disease, or the predisposition toward the disease.

Alleviating the tissue fibrosis and/or injury and/or organ failure occurred in kidney such as kidney fibrosis or the tissue fibrosis and/or injury and/or organ failure occurred in lung such as pulmonary fibrosis includes delaying the development or progression of the disease, or reducing disease severity. Alleviating the disease does not necessarily require curative results. As used therein, "delaying" the development of a disease (such as tissue fibrosis and/or injury and/or organ failure) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of tissue fibrosis and/or injury and/or organ failure includes initial onset and/or recurrence.

In some embodiments, the IL-24 protein or the interleukin 20 antagonist described herein is administered to a subject in need of the treatment at an amount sufficient to reduce the level of the activity of serum creatinine and BUN serum creatinine and BUN or TGFβ and αSMA expression in the subject by at least about 20% (e.g., 30%, 40%, 50%, 60%, 70%, 80%, 90% or greater). In other embodiments, the amount of the IL-24 protein or the interleukin 20 antagonist used in the treatment is sufficient to prolong the survival rate of the patient. Alternatively or in addition, the amount of the IL-24 protein or the interleukin 20 antagonist is sufficient to reduce one or more fibrosis and/or inflammatory factors (e.g., TGF-β, α-SMA, MIP-20, TIMP-1, MCP-1, IL-1β, KC and TNF-α) by at least about 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, intraperitoneal, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the IL-24 protein or the interleukin 20 antagonist and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the IL-24 protein or the interleukin 20 antagonist, can be dissolved and administered in a pharmaceutical excipient such as Water-for-Injection, 0.9% saline, or 5% glucose solution.

In one embodiment, an IL-24 protein or the interleukin 20 antagonist is administered via site-specific or targeted local delivery techniques. Examples of site-specific or targeted local delivery techniques include various implantable depot sources of the IL-24 protein or the interleukin 20 antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The therapeutic IL-24 proteins or the interleukin 20 antagonist described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the IL-24 proteins or the interleukin 20 antagonist. The particular dosage regimen, i.e., dose, timing and repetition, used in the method described herein will depend on the particular subject and that subject's medical history.

Treatment efficacy can be assessed by methods well-known in the art, e.g., monitoring the levels of AST and/or ALT in a patient subjected to the treatment. See, e.g., Example 1 below. See also U.S. Pat. No. 8,603,470.

IV. Kits

The present disclosure also provides kits for use in alleviating the tissue fibrosis and/or injury and/or organ failure occurred in kidney such as kidney fibrosis or the tissue fibrosis and/or injury and/or organ failure occurred in lung such as pulmonary fibrosis. Such kits can include one or more containers comprising an IL-24 protein (such as those described herein) or the interleukin 20 antagonist. In some embodiments, the IL-24 protein or the interleukin 20 antagonist is a human protein.

In some embodiments, the kit can comprise instructions for use in accordance with any of the methods described herein. The included instructions can comprise a description of administration of the IL-24 protein or the interleukin 20 antagonist to treat, delay the onset, or alleviate the tissue fibrosis and/or injury and/or organ failure according to any of the methods described herein. The kit may further comprise a description of selecting an individual suitable for treatment based on identifying whether that individual has a target disease. In still other embodiments, the instructions comprise a description of administering an IL-24 protein to an individual at risk of the disease.

The instructions relating to the use of an IL-24 protein or the interleukin 20 antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating tissue fibrosis and/or injury and/or organ failure. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-24 protein or the interleukin 20 antagonist.

Kits may optionally provide additional components such as buffers and interpretive information. Normally, the kit comprises a container and a label or package insert(s) on or associated with the container. In some embodiments, the invention provides articles of manufacture comprising contents of the kits described above.

V. Combined Therapy

Any of the IL-24 proteins or the interleukin 20 antagonist described herein can be used in combination with one or more additional pharmaceutical agents (e.g., therapeutically and/or prophylactically active agents) useful in treating and/or delaying the onset of tissue fibrosis and/or injury and/or organ failure, including those described herein. The IL-24 protein or the interleukin 20 antagonist or compositions containing such can be administered in combination with the additional pharmaceutical agents that improve their activity (e.g., activity, including potency and/or efficacy) in treating and/or reducing the risk for a target tissue fibrosis and/or injury and/or organ failure in a subject in need thereof, improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including an IL-24 protein or the interleukin 20 antagonist as described herein and an additional pharmaceutical agent shows a synergistic effect that is absent in a pharmaceutical composition including one of the IL-24 protein or the interleukin 20 antagonist and the additional pharmaceutical agent, but not both.

An IL-24 protein or the interleukin 20 antagonist or a combination containing such can be administered concurrently with, prior to, or subsequent to the one or more additional pharmaceutical agents (e.g., therapeutically active agents or prophylactically active agents), which may be useful as, e.g., combination therapies in treating and/or reducing the risk for the tissue fibrosis and/or injury and/or organ failure such as those described herein. Pharmaceutical agents include small organic molecules such as drug compounds or co-crystals thereof (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric or glucose or lipid metabolic disorder in a subject. In certain embodiments, the additional pharmaceutical agent is a pharmaceutical agent approved by a regulatory agency (e.g., the US FDA) for treating and/or reducing the risk for a tissue fibrosis and/or injury and/or organ failure as described herein in a subject. Each additional pharmaceutical agent may be administered at a dose and/or on a time schedule determined for that pharmaceutical agent. The additional pharmaceutical agents may also be administered together with each other and/or with the IL-24 protein or the interleukin 20 antagonist or a composition containing such in a single dose or administered separately in different doses. The particular combination to employ in a regimen will take into account compatibility of the IL-24 protein or the interleukin 20 antagonist described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: IL-24 Treating the Tissue Fibrosis and/or Injury and/or Organ Failure Occurred in Kidney Materials and Methods
Reagents Antibodies against IL-24 (303308) and (MA5-27141) were purchased from Invitrogen. Antibody against IL-20 (7E) was prepared as previously described (Wei, C. C., et al., *Detection of IL-20 and its receptors on psoriatic skin*. Clin Immunol, 2005. 117(1): p. 65-72). Antibodies against α-SMA (ab124964) and N-cadherin (ab18203) were purchased from Abcam. Antibody against TGF-β (18978-1-AP), β-actin (20536-1-AP) and E-cadherin (20874-1-AP) were purchased from Proteintech.

Clinical Specimens

The protocol of clinical study conformed to the ethical guidelines of the 1975 Declaration of Helsinki and was approved by the Ethics Committee of National Cheng Kung University Hospital (IRB No: B-ER-108-068). Renal biopsies were collected from patients. Written informed consent was obtained from each patient.

Immunofluorescence (IF)

The expression of α-SMA was also assessed using IF staining. Cell culture were prepared for immunofluorescence staining with the α-SMA antibody (Abcam, ab164964) at 4° C. overnight. At the second day, they were incubated for 2 h with Alexa Fluor®594-conjugated goat-anti-rabbit secondary antibody (Jackson ImmunoResearch Laboratories, USA), and finally mounted with DAPI (Vector Laboratories, Peterborough, UK). We applied IF staining to analyze the expression levels of the activated myofibrolast marker—α-SMA. Images were photographed using a digital microscope camera (DP12; Olympus Co., Tokyo, Japan).

Immunohistochemistry (IHC)

Paraffin sections of renal biopsies obtained from patients with CKD (n=5), were used for IHC staining with the anti-IL-24 antibody (Invitrogen, MA5-27141). Sections incubated with mIgG isotype (clone 11711; R&D Systems, Minneapolis, Minn.) were used as negative control. The protein expression of IL-24 was quantified by the HistoQuest as mean intensity (pixel). IHC staining was performed to analyze the expression levels of TGF-β and α-SMA in the mice renal tissues. Briefly, paraffin sections were incubated with primary antibody against TGF-β (Proteintech, 18978-1-AP) or α-SMA (Abcam, ab124964) 4° C. overnight. The next day, the sections were washed with PBS and incubated with the secondary antibody for one hour. The reaction was detected using AEC chromogen stain, and the nuclei were counterstained with hematoxylin.

Flow Cytometry Analysis

For analysis of macrophage surface markers expression, APC-, PE- and FITC-conjugated Abs anti-mouse CD80, CD206 and F4/80 were used. Mouse isotype controls were also used. The cells were washed and stained for 1 hour at 4° C. with the optimal dilution of each antibody. Cells were washed again and analyzed by flow cytometry (Cytoflex™, Beckman Coulter). Data analysis was done using FlowJo software (Ashland, OR). All assays were repeated at least three independent times.

Animal Experiments 6- to 8-weeks old C57BL/6 JNarl wild-type mice were purchased from National Laboratory Animal Center were (National Cheng Kung University, Tainan, Taiwan). All animal experiments were conducted according to the protocols based on the National Institutes of Health standards and guidelines for the care and use of experimental animals.

Sample Collection and Serum Biochemistry

Blood was collected via retro-orbital sinus puncture or cardiac puncture. Centrifuged with 3500 rpm for serum. Serum was frozen at −80° C. for the analysis of creatinine and blood urea nitrogen (BUN) with an automatic biochemical analyzer (Olympus).

Real-Time PCR

Total RNA was extracted from frozen renal samples using Trizol reagent and reverse transcription was performed with reverse transcriptase (PrimeScript RT-PCR kit) according to the manufacturer's protocol. The expression levels of Cdh1 (E-cadherin), Cdh2 (N-cadherin), Tgfb (TGF-β), Acta2 (α-SMA), Col1a1 (Collagen-1), Cspg4 (NG2), Dem (Desmin), Vim (Vimentin), Nos2 (iNOS), Arg1 (Arginase), Tnfa (TNF-α), Il1B (IL-1β), Il6 (IL-6), Il11 (IL-11), Il20 (IL-20) and Il24 (IL-24) were amplified on a StepOne-Plus™, with SYBR Green (Applied Biosystem) for quantitative analysis normalized with Glyceraldehyde phosphate dehydrogenase (Gapdh), as internal control. Relative multiples of change in mRNA expression were determined by calculating 2-ΔΔCt.

Expression and Purification of Mouse IL-24

Mouse Il24 mRNA was isolated from murine HCC ML-14a cell line (The Food Industry Research and Development Institute, Taiwan). The recombinant plasmid pET22b-IL-24 was transformed into BL21 competent cells (Life Technologies). The enriched inclusion body was re-suspended and passed through the Q column (GE Healthcare). The flow-through was collected and filtrated through a 0.22-μm Millipore filter (Millipore).

Cell Culture and Experiments

Mouse renal epithelial cell line (M-1) was used in this study. The cell proliferation of the M-1 was assessed by the MTT assay. Briefly, cells were treated with PBS or mouse IL-24 protein (400 ng/ml), the MTT reagent (Sigma-Aldrich) was added after 24. Two hours after the addition of MTT reagent, the MTT formazan was dissolved in DMSO and measured at OD550 nm.

Unilateral Ureteral Obstruction (UUO)-Induced Renal Fibrosis

In UUO-induced renal fibrosis animal model, the wide-type male mice (C57BL/6J) and IL-20R1-deficient mice used in this study were between 8 and 10 weeks old (n≥5 per experimental group). Short-term was induced 2 weeks and Long-term was induced 4 weeks. For testing the effects of IL-24 on long-term model, mice were given recombinant mouse IL-24 protein (1 mg/kg) at 24 hr after UUO surgery. IL-24 protein was injected twice a week for 4 weeks. Renal sections from sacrificed animals were preserved in formalin and processed in paraffin tissue-processing method or immediately frozen in liquid nitrogen and stored for RNA extraction. Sirius red stain were applied to analyze renal fibrosis and the deposition of collagen.

Statistical Analysis

Data are expressed as means±standard error of the mean (SEM). Differences between two groups were assessed using the unpaired two-tailed Student's t-test. P<0.05 was considered statistically significant. All data were collected in Microsoft Excel (Microsoft Inc.) and GraphPad Prism 6.

Results

IL-24 Down-Regulated and Associated with Renal Fibrosis in CKD.

To investigate the association of IL-24 with CKD in clinics, we analyzed the expression levels of IL-24 in the renal tissue from patients with CKD. Immunohistochemistry (IHC) staining showed that IL-24 was strongly expressed at the region of renal tubular epithelial cells (FIG. 1A). However, the expression of IL-24 was downregulated in the fibrotic area (black arrow). The results indicated IL-24 was mainly expressed in renal tubules, but downregulated in the fibrotic region.

Figure 1B:
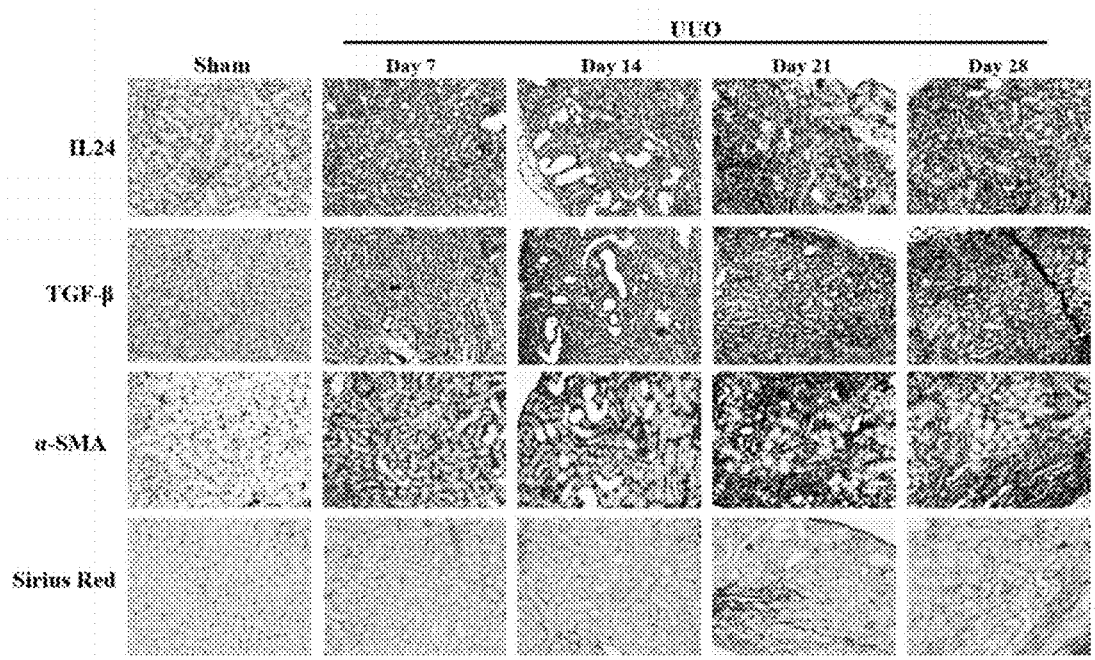
FIG. 1B: Immunohistochemistry was used to detect the expression level of IL-20, IL-24, TGF-β, α-SMA and Sirius red stain was used to analyze the deposition of collagen. Original magnification: 200× and 400×.
Figure 1C:
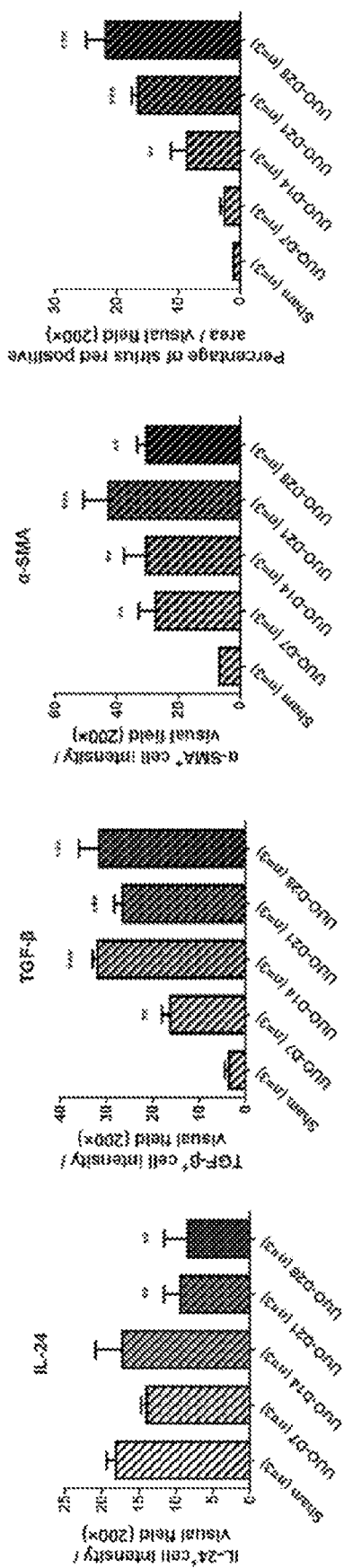
FIG. 1C: Quantification of IL-24, TGF-β, α-SMA, comparing with sham control.
Figure 1D:
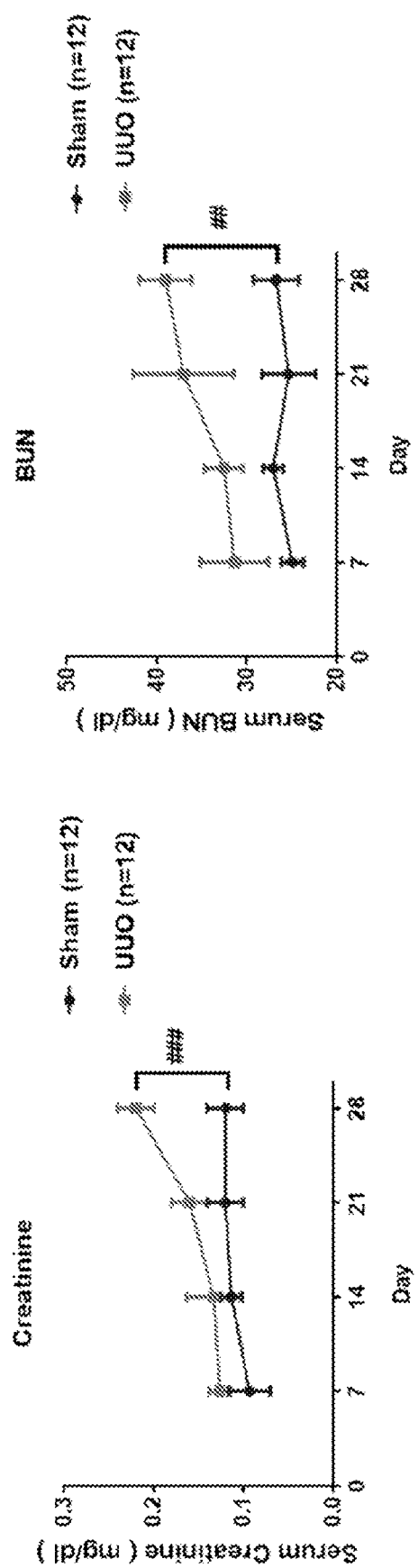
FIG. 1D: Serum levels of creatinine and blood urea nitrogen (BUN) were detected by the time after UUO surgery. *P<0.05, P<0.001, *P<0.001 compared with Sham group.

To further investigate the dynamic expression profiles of IL-24 in the progression of renal fibrosis in vivo, we established Unilateral Ureteral Obstruction (UUO) model of murine with renal fibrosis. Several fibrotic proteins and IL-24 were involved in UUO mice. Immunohistochemistry staining showed that TGF-β and α-SMA, which were recognized as a major driver of fibrosis, were highly expressed after UUO surgery (FIG. 1B, 1C). Sirius red staining was applied to visualize collagen fibers. Levels of collagen deposition in renal interstitial tissue were gradually higher in UUO mice. However, IL-24, which was mainly expressed in renal tubules, was significantly downregulated after day 21 (FIG. 1B). In addition, the renal function deteriorated as indicated by increase of serum creatinine and BUN (FIG. 1D). These data showed we successfully established renal fibrosis model by UUO surgery and IL-24 diminished after renal injury.

IL-24 Administration Protected Mice Against Renal Fibrosis in Long-Term UUO.

Figure 2A:
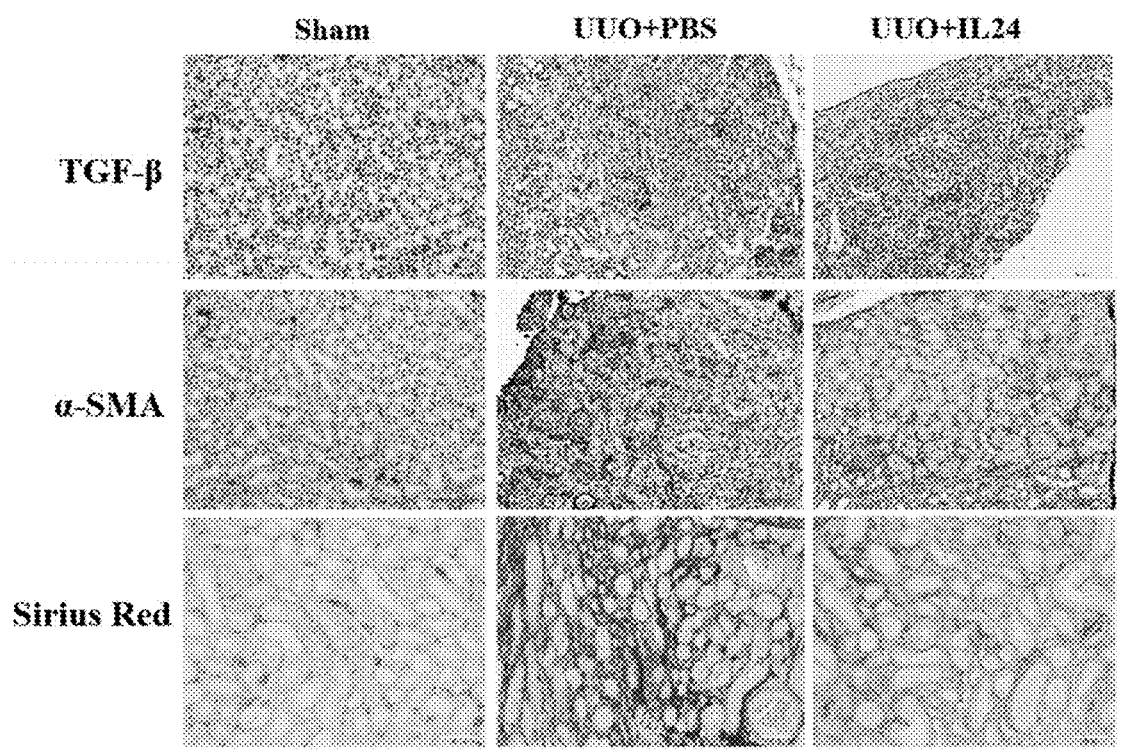
FIG. 2A: Immunohistochemistry was used to detect the expression level of fibrogenic factor—TGF-β, α-SMA and Sirius red stain was used to analyze the deposition of collagen in long-term UUO mice. Original magnification: 200× and 400×.
Figure 2B:
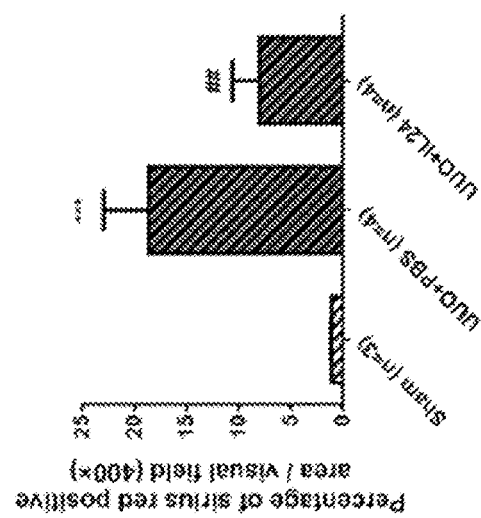
FIG. 2B: Quantification of TGF-β, α-SMA expression and collagen deposition in renal tissue.
Figure 2B:
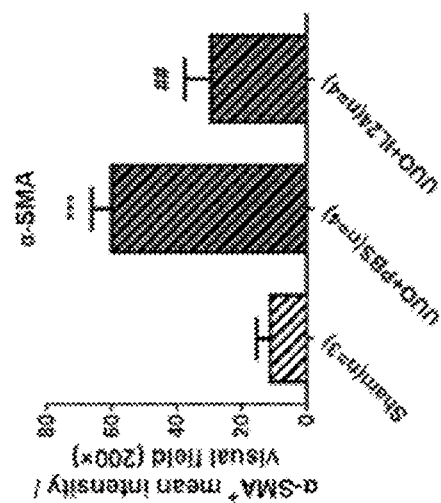
Figure 2B:
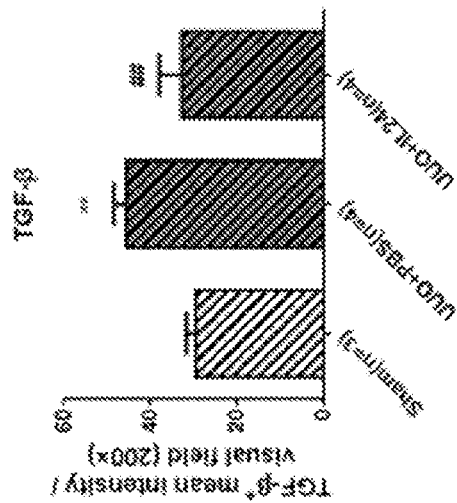
Figure 2C:
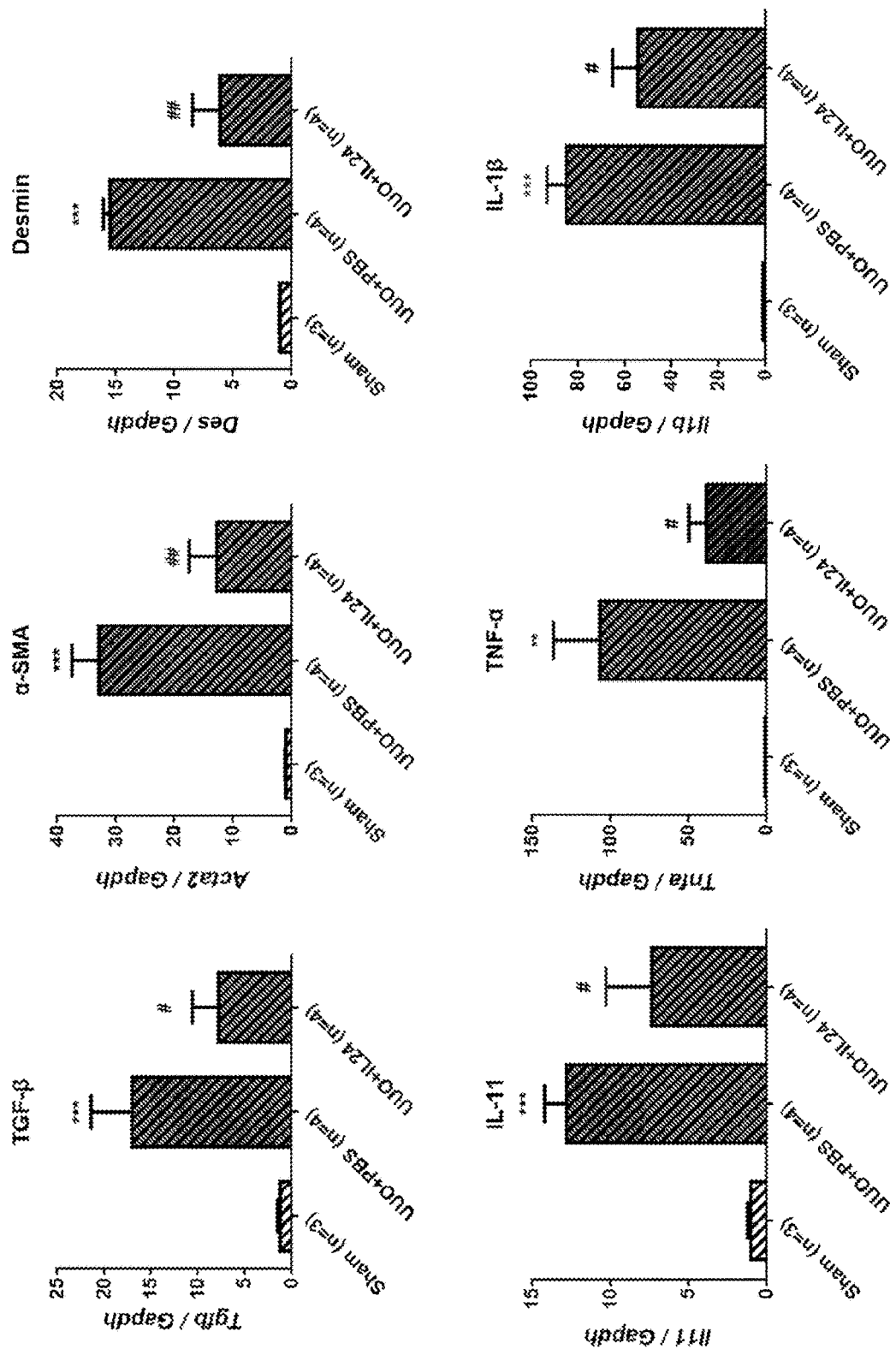
FIG. 2C: The mRNA transcripts of Tgfb, Acta2, Il11, Il1b, Il6, and Tnfa were analyzed using real-time PCR with specific primers. Gapdh was used as an internal control.
Figure 2D:
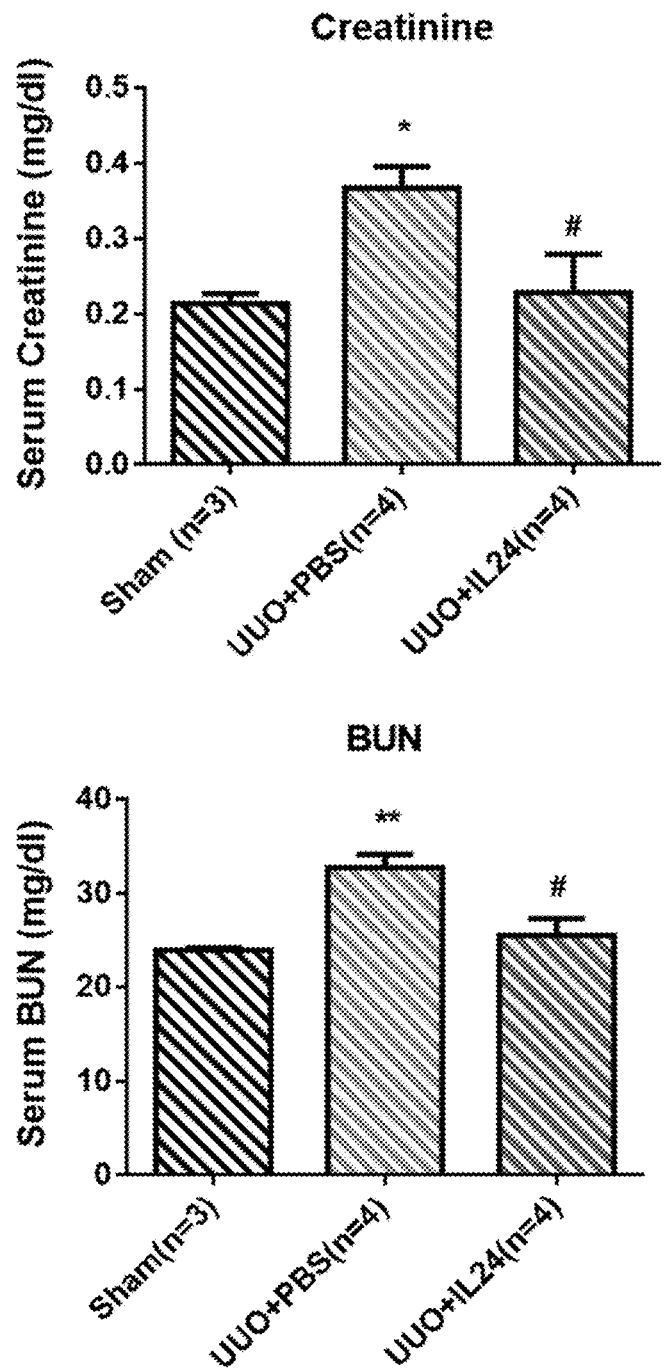
FIG. 2D: Serum levels of creatinine and blood urea nitrogen (BUN) were detected to assess the renal function. Data are means±SEM. *P<0.05, P<0.001, *P<0.001 compared with Sham group, #P<0.05, ##P<0.01, ###P<0.001 compared with UUO+PBS group.

In order to investigate the role of IL-24 in renal fibrosis, we analyzed the effects of IL-24 on the disease model of renal fibrosis. Mice were treated with IL-24 recombinant protein 24 hours after UUO surgery. We administered IL-24 at 1 mg kg$^{-1}$ intraperitoneally twice per week. IL-24-treated mice showed a reduction of the collagen accumulation compared to that in the control group via Sirius Red staining (FIGS. 2A, 2B). The protein level of α-SMA and TGF-β, fibrotic factors of the renal were also downregulated in the IL-24-treated group (FIG. 2B). The mRNA expression of Tgfb, Acta2, Il11, Des, Il1b and Tnfa were significantly downregulated in the IL-24-treated mice (FIG. 2C). In addition, the renal function indicated by serum levels of creatinine and BUN, was protected in the group of IL-24 treatment compared to PBS-treated with UUO (FIG. 2D). These results suggested that IL-24 potentially prevents renal against renal fibrosis with mice.

Figure 3A:
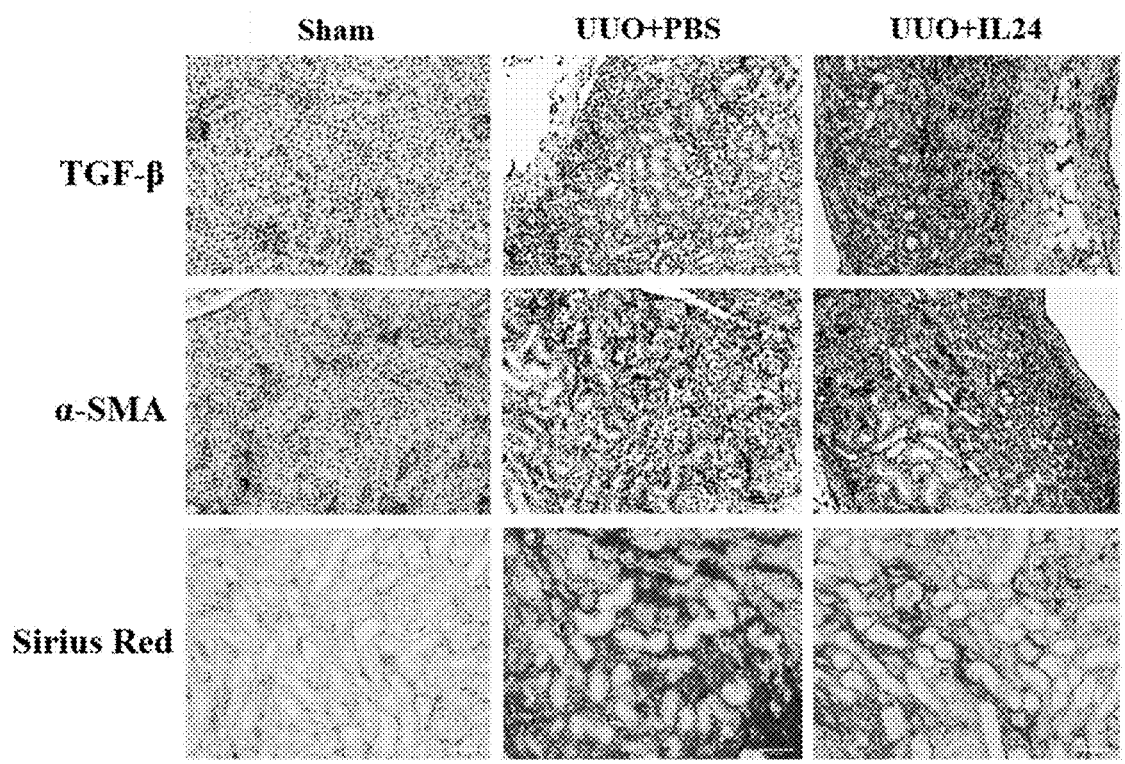
FIG. 3A: Immunohistochemistry was used to detect the expression level of fibrogenic factor—TGF-β, α-SMA and Sirius red stain was used to analyze the accumulation of collagen in long-term UUO-induced renal fibrosis model. Original magnification: 200× and 400×.
Figure 3B:
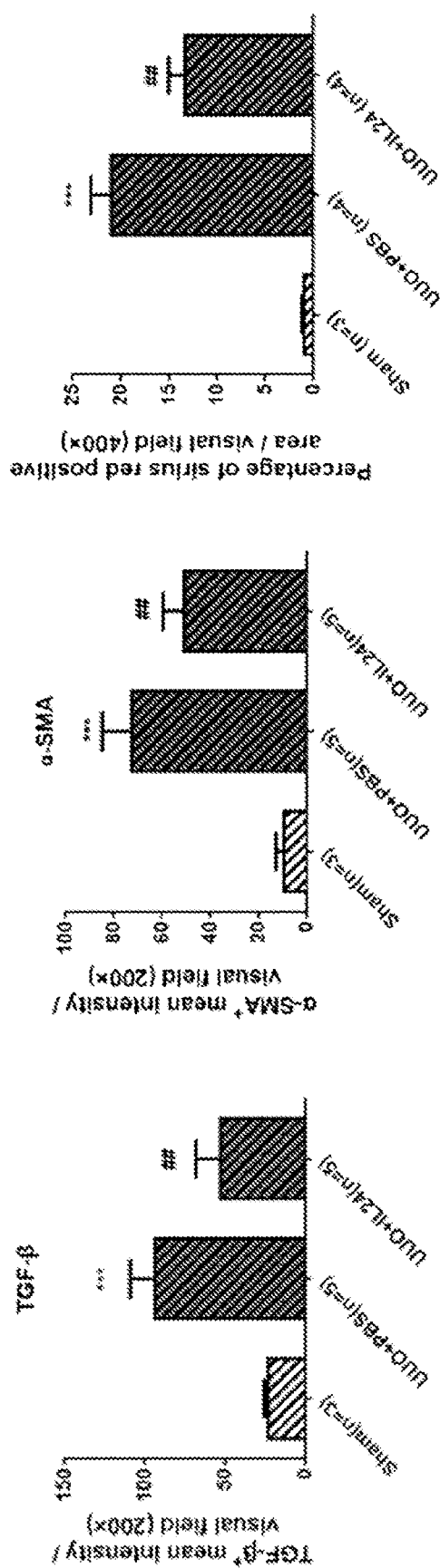
FIG. 3B: Quantification of TGF-β, α-SMA expression and collagen deposition in renal tissue.
Figure 3C:
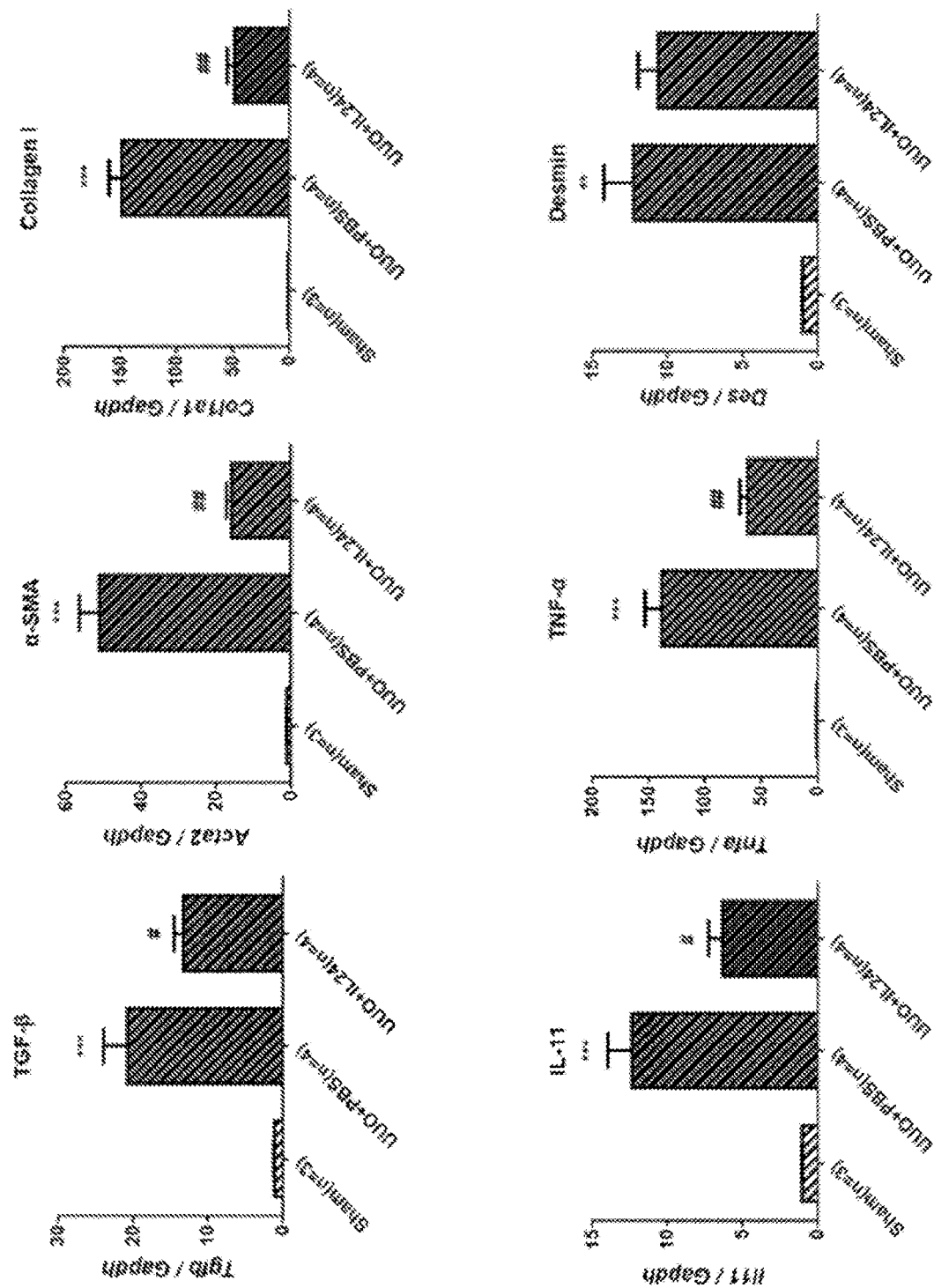
FIG. 3C: The mRNA transcripts of Tgfb, Acta2, Il11, Dcn, Il1b, and Col1a1 were analyzed using real-time PCR with specific primers.
Figure 3D:
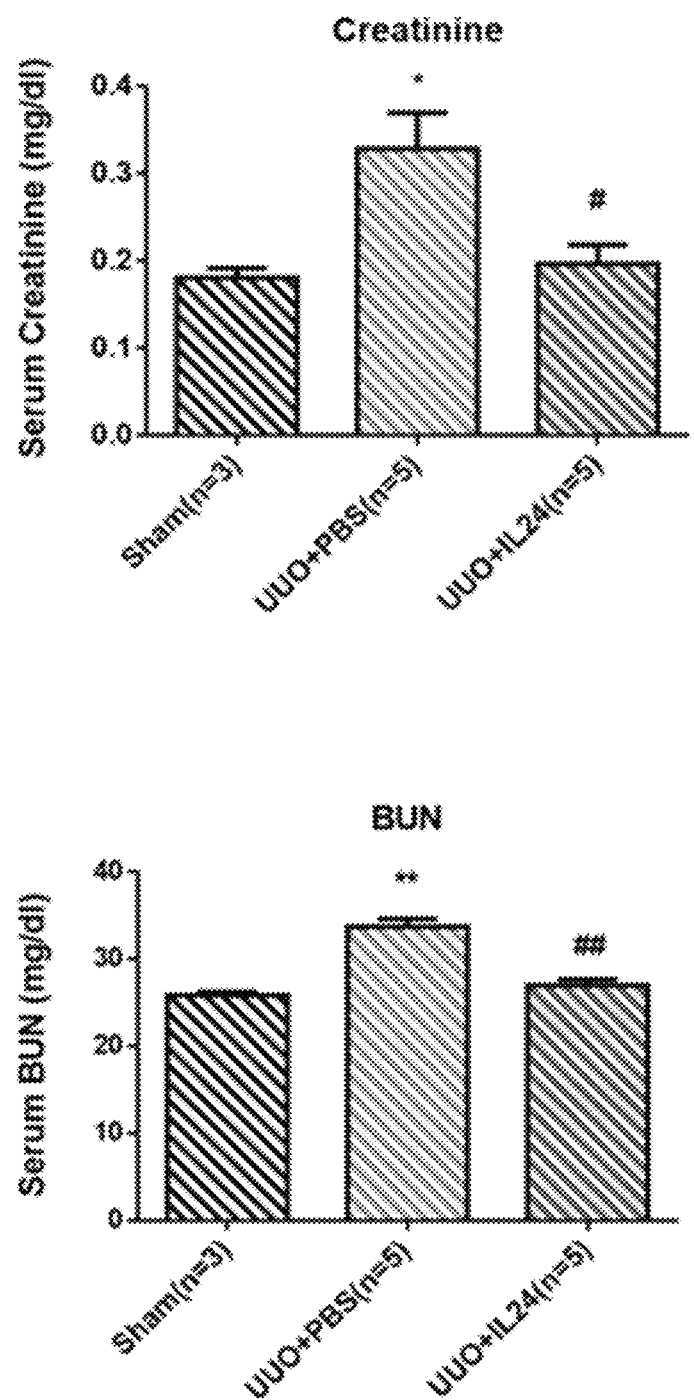
FIG. 3D: Serum creatinine and blood urea nitrogen (BUN) were measured after treatment of IL-24. Gapdh was used as an internal control. Data are means±SEM. *P<0.05, P<0.001, *P<0.001 compared with Sham group, #P<0.05, ##P<0.01, ###P<0.001 compared with UUO+PBS group.

Base on the dynamic of UUO surgery, the excessive collagen was accumulated on the kidney parenchyma 14 days via Sirius Red staining. To determine whether IL-24 also have efficacy as a therapeutic drug after the renal is fibrotic, we treated the mice with IL-24 protein after 2 weeks of UUO surgery to determine the effect of IL-24 on renal fibrosis. The result showed that IL-24-treated mice diminished UUO-induced renal fibrosis, decreased the expression of pro-fibrogenic factors, reduction of collagen production (FIGS. 3B, 3C) and maintained renal function (FIG. 3D). Therefore, IL-24 also had a therapeutic effect after renal injury has occurred. We conclude that IL-24 had significant protective and therapeutic effect on renal fibrosis.

IL-24-Treated Mice were Resistance to Doxorubicin-Induced Renal Injury

Figure 4A:
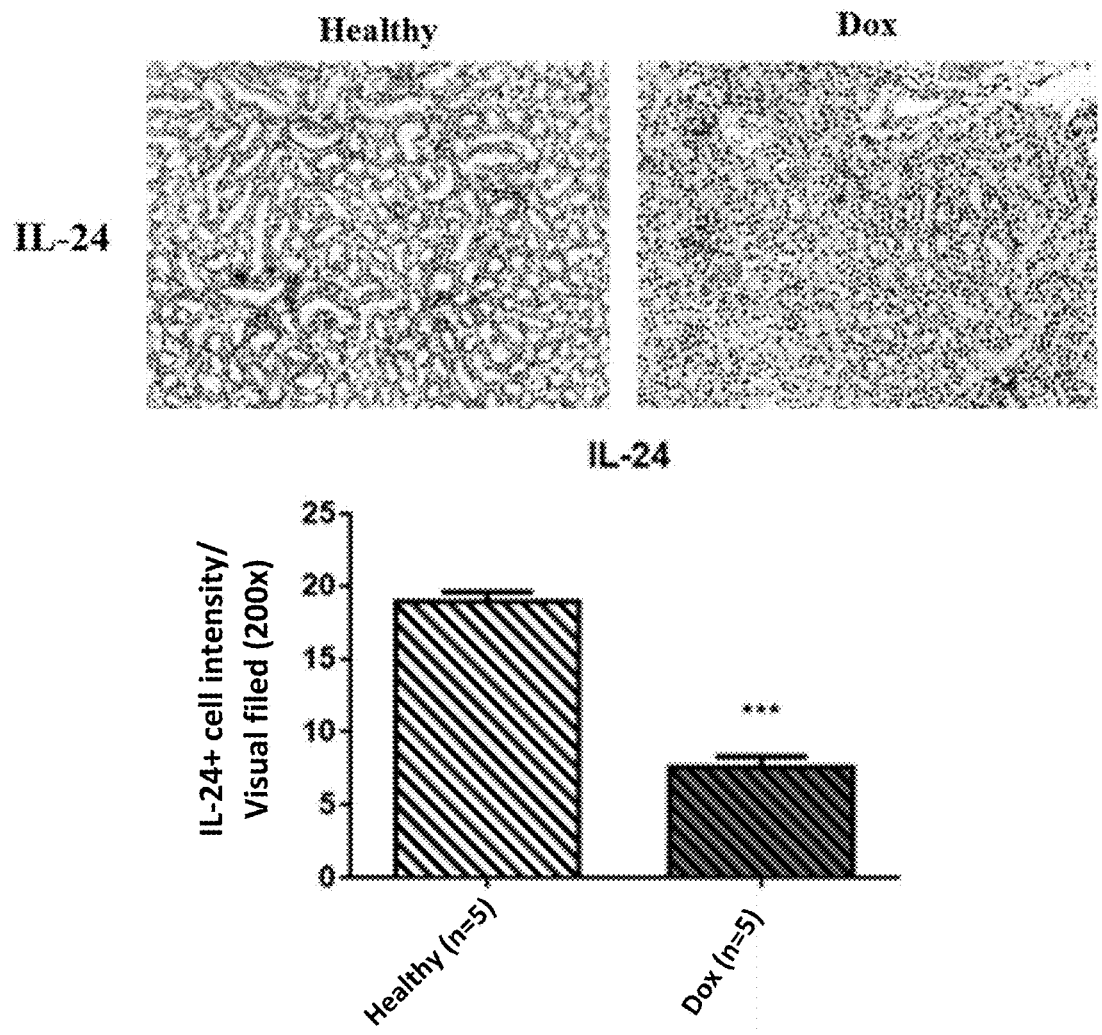
FIG. 4A: Immunohistochemistry was used to detect the expression level of IL-24 and quantification.
Figure 4B:
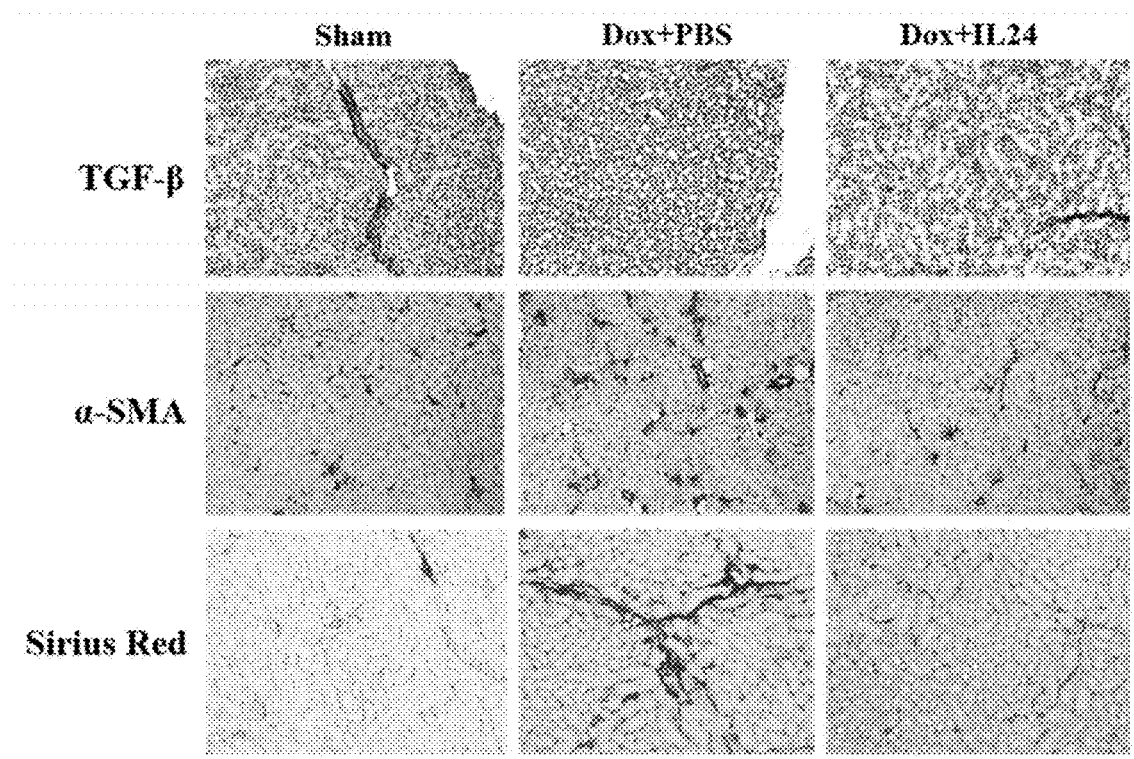
FIG. 4B: IHC was used to detect the expression level of fibrogenic factor—TGF-β, α-SMA and Sirius red stain was used to analyze the accumulation of collagen. Original magnification: 200×.
Figure 4C:
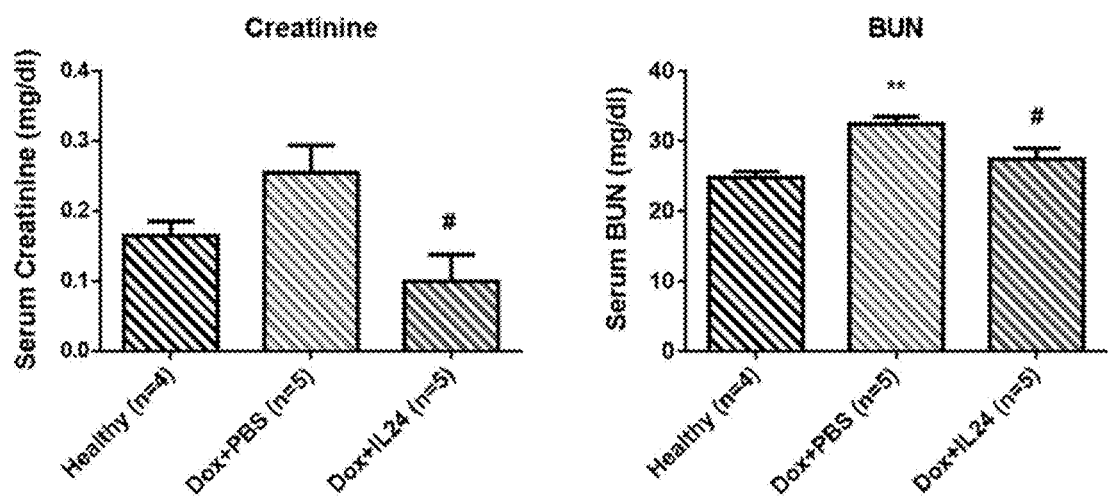
FIG. 4C: Serum creatinine and blood urea nitrogen (BUN) were measured after treatment of IL-24. Data are means±SD. *P<0.05, P<0.001, *P<0.001 compared with Dox group, #P<0.05, ##P<0.01, ###P<0.001 compared with treatment of Dox+PBS group.

In clinical, Doxorubicin (DOX) is a commonly used chemotherapy drug for human cancers, however it may cause serious side effects which include heart damage and nephrotoxicity (Mitry, M. A. and J. G. Edwards, Doxorubicin induced heart failure: Phenotype and molecular mechanisms. Int J Cardiol Heart Vasc, 2016. 10: p. 17-24; Octavia, Y., et al., Doxorubicin-induced cardiomyopathy: from molecular mechanisms to therapeutic strategies. J Mol Cell Cardiol, 2012. 52(6): p. 1213-25; Rea, D., et al., Strain Analysis in the Assessment of a Mouse Model of Cardiotoxicity due to Chemotherapy: Sample for Preclinical Research. In Vivo, 2016. 30(3): p. 279-90). To evaluate whether the effect of IL-24 act as a protection role in the renal, we analyzed the expression of IL-24 on DOX-induced animal model. Immunohistochemistry staining showed that IL-24 was involved in the renal tissue and downregulated on tubular epithelial cells of renal tissue in DOX-induced mice (FIG. 4A). To further prove whether IL-24 also have efficacy in protection after renal injury, we treated DOX-induced mice with injection of IL-24 at 1 mg kg$^{-1}$ twice per week after 14 days to determine the effect of IL-24 on nephrotoxicity. IL-24-treated mice showed protection against renal damage, downregulated the expression of pro-fibrogenic factors, decreased collagen accumulation (FIG. 4B) and the function of renal was also maintained (FIG. 4C). Therefore, IL-24 had a protection effect of renal tissue after renal injury.

Example 2: IL-24 Treating the Tissue Fibrosis and/or Injury and/or Organ Failure Occurred in Lung Materials and Methods
Animal Seven-week-old C57BL/6J female mice were purchased from National Cheng Kung University Animal Center, and kept on a 12-hour light-dark cycle at 22±2° C. Animals were kept in independent ventilation sterile feeding cages (IVC) and were given standard drinking water and feed. All animal experiments were conducted according to the protocols based on the Taiwan National Institutes of Health (Taipei, Taiwan) standards and guidelines for the care and use of experimental animals. The Animal Ethics Committee of National Cheng Kung University approved the research procedures. The methods were carried out in accordance with the approved guidelines. All efforts were made to minimize animal suffering and to reduce the number of animals used. For all procedures, anesthesia was achieved by intraperitoneal injection of standard dosages of pentobarbital.

Treatment

Each mouse were treated with 50 μg (in 50 μl saline) bleomycin (Nippon Kayaku Co., Ltd.) by intratracheal instillation after anesthesia. IL-24 was given by intraperitoneal injection (1 mg/kg, n=5) into mice 24 hours before the treatment of bleomycin, and following by two injections per week. Mice treated with PBS were used as the control group. Anti-IL-20 antibody (7E) (3 mg/kg, n=3) was given 1 hour after the treatment of bleomycin, and following by twice injection a week. Mouse IgG isotype control (3 mg/kg, n=3). Three weeks after the treatment of bleomycin, the pulmonary function of mice was analyzed.

Pulmonary Respiratory System Function Measurement

The pulmonary function of the mice were measured by the FlexiVent respirator (SCIREQ). First, mice were given pentobarbital without affecting their breathing. A hose was inserted into its trachea and connected to the machine. The atomized nozzle gave PBS to the trachea, and the machine used different vibration methods to calculate the parameters by computer software. Finally, we obtained the changes of pulmonary function in mice.

Immunohistochemistry (IHC)

IHC staining was performed to analyze the expression level of α-SMA in the mice lung. Briefly, paraffin sections were incubated with primary antibody against α-SMA (Abcam, ab124964) 4° C. overnight. The next day, the sections were washed with PBS and incubated with the secondary antibody for one hour. The reaction was detected using AEC chromogen stain, and the nuclei were counterstained with hematoxylin.

Use of IL-24 or its Agonists and Anti-IL-20 Antibodies to Treat Fibrosis, any Injury and Organ Failures Pulmonary fibrosis is a chronic and progressive inflammatory disease. Due to the diagnosis is not easy, the discovery of pulmonary fibrosis is mostly end-stage with the high mortality rate. In recent years, the incidence rate continued to rise. At present, the causes of idiopathic pulmonary fibrosis (IPF) have not been understood. Congenital genetic or acquired environmental factors and aging may be the reasons. After the damage of alveolar epithelial cells, the activated fibroblasts produce excessive extracellular matrix (ECM), resulting in pulmonary fibrosis. Eventually, the lungs would lose their original elasticity, and the gradually thickened alveoli wall would lead to abnormal gas exchange. As a result, symptoms such as wheezing, dry cough, and dyspnea would occur, causing decreased pulmonary function. Up to now, there is still no effective radical drug for treating pulmonary fibrosis. Treatments for pulmonary fibrosis are mostly to prevent the continued deterioration. Therefore, it is unmet medical need to search novel drugs for treating IPF.

Bleomycin is a clinical anti-cancer drug for treating head and neck cancer, germ cell tumors, and lymphoma. As a glycol-peptide antibiotic derived from *Streptomyces verticillus*, bleomycin has serious side effects which causes inflammation in the lungs and eventually leads to fibrosis. Due to the lack of bleomycin hydrolysis enzymes in the lungs, bleomycin has the pulmonary toxicity which leads to damage on epithelial cells. Currently, a lot of studies use bleomycin to develop pulmonary fibrosis murine model. After three weeks of the treatment of bleomycin, severe pulmonary fibrosis would be observed.

Interleukin-24 (IL-24) and interleukin-20 (IL-20) are members of the interleukin-10 family, which share the same receptors, IL-20R1/IL-20R2 and IL-20R2/IL-22R1. Both of them are involved in many inflammatory diseases. IL-24 is considered to be an important pleiotropic immune-regulatory cytokine. IL-24 is able to fight against melanoma cells and causes cell apoptosis and has no effect on normal cells. IL-20 is a pro-inflammatory cytokine involved in the pathogenesis of various inflammatory diseases, such as rheumatoid arthritis, osteoporosis. However, the role of IL-24 and IL-20 in pulmonary fibrosis has not been discussed. In this study, we will investigate the therapeutic effects of IL-24 and anti-IL-20 monoclonal antibody (7E) in the pulmonary fibrosis murine model.

Given the above, we confirmed that IL-24 and IL-20 were indeed involved in the pulmonary fibrosis through our in vivo data. Administering IL-24 or anti-IL-20 antibody (7E) treatment can effectively protect the pulmonary function of mice from bleomycin. It was also observed in pathological tissues that IL-24-treated group had smaller fibrotic areas and decrease of the fibrogenic factor (α-SMA). We will further explore its mechanism of action through in vitro experiments. In summary, the results demonstrated that IL-24 and anti-IL-20 monoclonal antibody (7E) might be therapeutic agents in the treatment of pulmonary fibrosis.

IL-24 or Anti-20 Antibody Decreased the Fibrotic Area and Inhibited the Production of Fibrogenic Factors in the Lung In order to effectively and quickly realize whether IL-24 or IL-20 is involved in pulmonary fibrosis, we use bleomycin to establish a murine pulmonary fibrosis model. IL-24 or anti-20 antibody was administered through i.p. injection to test as a therapeutic potential. Based on the results, IL-24 and anti-20 antibody significantly reduced the lung fibrosis area, and inhibited the expression of several fibrotic factors.

Figure 5:
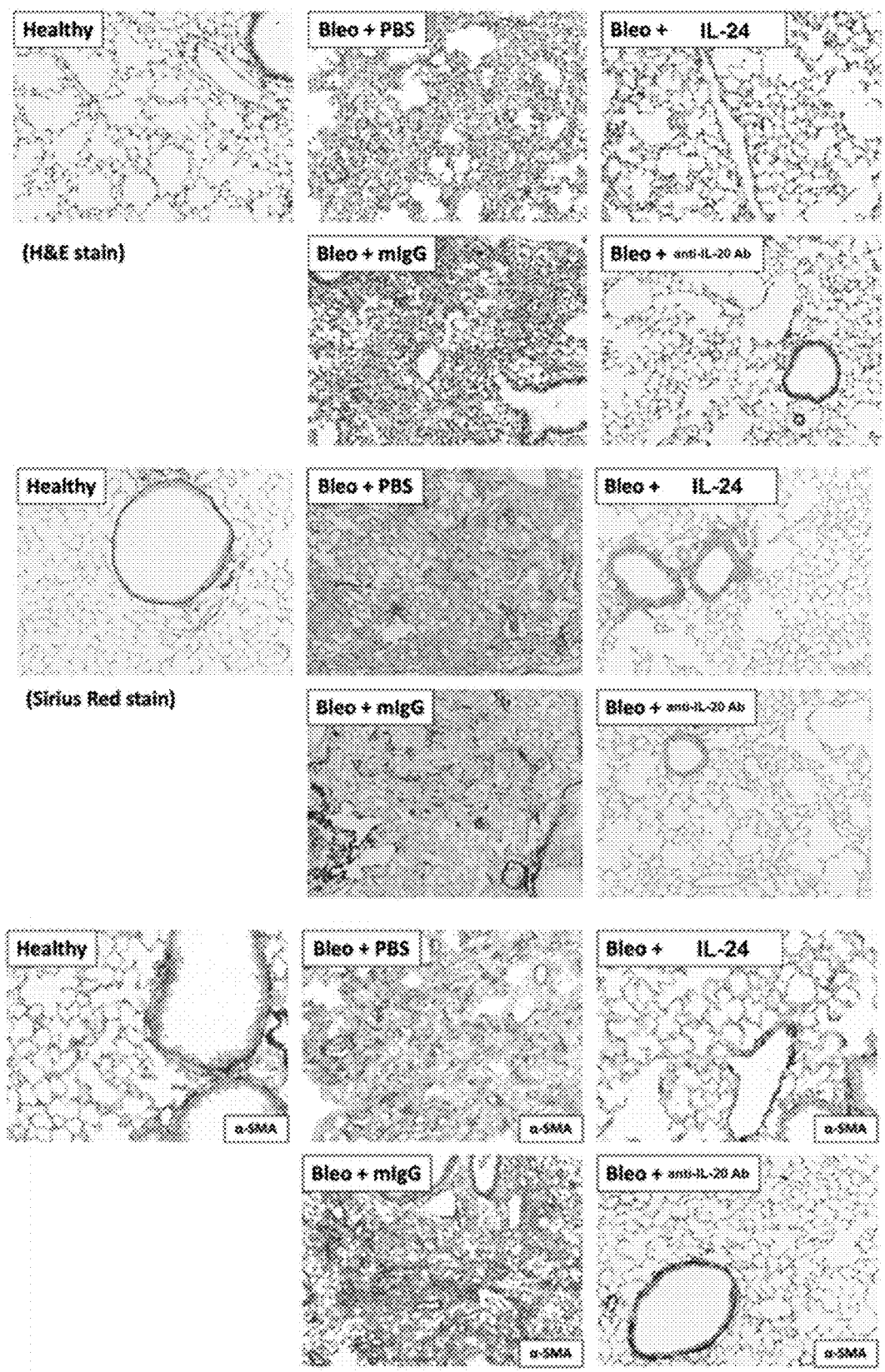
FIG. 5: Representative images of hematoxylin and eosin stain, immunostaining and Sirius Red staining for the deposition of collagen in lung tissue from mouse model with bleomycin treatment and healthy controls.

Through hematoxylin and eosin stain as shown in FIG. 5, we observed a significant thickening of lung tissue in mice with bleomycin, which is considered a hallmark of fibrosis. In the IL-24 treated and the anti-20 antibody-treated groups, the morphology were more similar to the healthy group without excessive tissue proliferation. We further to examine the expression of fibrogenic factors, alpha smooth muscle actin (α-SMA) and collagen, by immunohistochemistry and Sirius Red staining respectively. We observed cytokines A-treated and the anti-X antibody-treated groups had significant decreases in the production of α-SMA and collagen.

IL-24 or Anti-20 Antibody Protects Pulmonary Function of Mice from the Injury of Bleomycin We found that IL-24 diminished in the fibrotic lung and IL-20 increased in the fibrotic lung compared to the healthy control lung. Therefore, we speculated that IL-24 may play a protective role, while IL-20 may play a detrimental (inflammatory) role in the pathogenesis of lung fibrosis.

Figure 6:
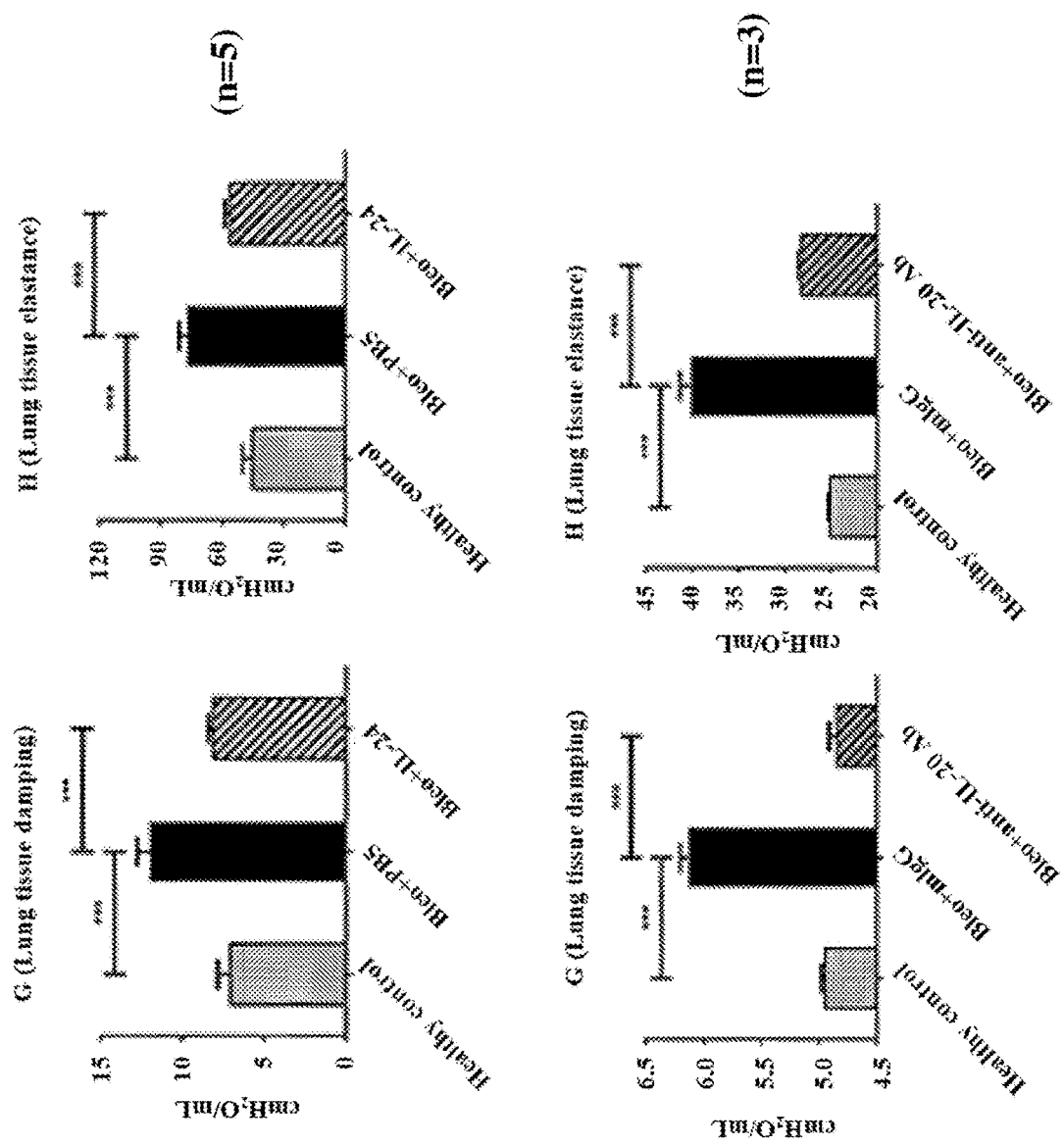
FIG. 6: In the pulmonary fibrosis model, the pulmonary function of mice was measured by FlexiVent respirator (SCIREQ). All functional indices in bleomycin (combined with PBS or IgG) groups were higher than the healthy group, indicating the decrease of the pulmonary function. Both cytokines 24-treated and the anti-20 antibody-treated mice showed the protection against the bleomycin-induced pulmonary dysfunction. (* p<0.01,  p<0.01, * p<0.001, respectively).
Figure 6:
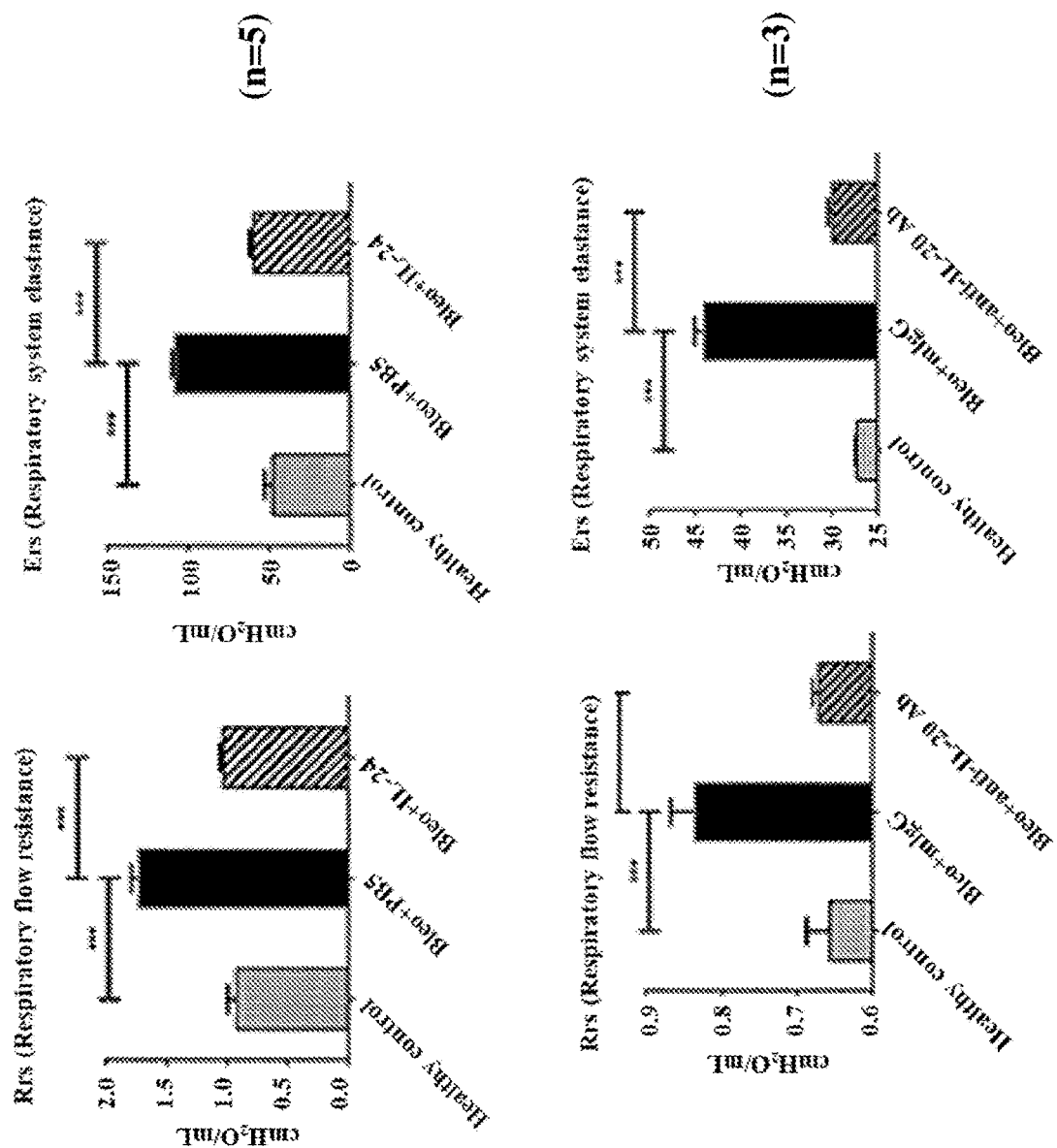

In order to effectively and quickly realize whether IL-24 or IL-20 is involved in pulmonary fibrosis, we use Bleomycin to establish a murine pulmonary fibrosis model. Interleukin-24 or anti-IL-20 antibody was administered through i.p. injection to test as a therapeutic potential. Based on the results shown in FIG. 6, IL-24 and anti-20 antibody significantly improved the pulmonary function.

While the following examples provide further detailed description of certain aspects and embodiments of the disclosure, they should be considered merely illustrative and not in any way limiting to the scope of the claims.

What is claimed is:

1. A method for alleviating or delaying the onset of or treating a tissue fibrosis occurred in kidney or lung, the method comprising administering an effective amount of an interleukin 24 (IL-24) protein to a subject in need thereof, wherein the IL-24 protein is a human IL-24 protein.

2. The method of claim 1, wherein the tissue fibrosis is kidney fibrosis.

3. The method of claim 2, wherein the kidney fibrosis is chemotherapy-induced renal fibrosis, which is doxorubicin-induced renal fibrosis.

4. The method of claim 1, wherein the tissue fibrosis is lung fibrosis.

5. The method of claim 4, wherein the lung fibrosis is chemotherapy-induced pulmonary fibrosis, which is bleomycin-induced pulmonary fibrosis.

6. The method of claim 4, wherein the lung fibrosis is antibiotic-induced pulmonary fibrosis, which is glycol-peptide antibiotic-induced pulmonary fibrosis.

7. The method of claim 1, wherein the subject is a human patient having or suspected of having the tissue fibrosis.

8. The method of claim 7, wherein the tissue fibrosis is renal fibrosis or pulmonary fibrosis.

9. The method of claim 1, wherein the human IL-24 protein is formulated in a pharmaceutical composition, which is administered to the subject by a systemic route.

10. The method of claim 9, wherein the pharmaceutical composition is administered parenterally.

11. The method of claim 10, wherein the pharmaceutical composition is administered via intravenous infusion or intraperitoneal injection.

* * * * *

SEQUENCE LISTING

```
<160> NUMBER OF SEQ ID NOS: 13

<210> SEQ ID NO 1
<211> LENGTH: 363
<212> TYPE: DNA
<213> ORGANISM: mouse
<220> FEATURE:
<221> NAME/KEY: CDS
<222> LOCATION: (1)..(363)

<400> SEQUENCE: 1 gaa ttg aag ctt gag gag tct gga gga ggc ttg gtg cag cct gga gga      48
Glu Leu Lys Leu Glu Glu Ser Gly Gly Gly Leu Val Gln Pro Gly Gly
1               5                   10                  15 tcc atg aaa ctc tct tgt gct gcc tct gga ttc act ttt agt gac gcc      96
Ser Met Lys Leu Ser Cys Ala Ala Ser Gly Phe Thr Phe Ser Asp Ala
            20                  25                  30 tgg atg gac tgg gtc cgc cag tct cca gag aag ggg ctt gag tgg att     144
Trp Met Asp Trp Val Arg Gln Ser Pro Glu Lys Gly Leu Glu Trp Ile
        35                  40                  45 gct gaa att aga agc aaa gct aat aat tat gca aca tac ttt gct gag     192
Ala Glu Ile Arg Ser Lys Ala Asn Asn Tyr Ala Thr Tyr Phe Ala Glu
    50                  55                  60 tct gtg aaa ggg agg ttc acc atc tca aga gat gat tcc aaa agt ggt     240
Ser Val Lys Gly Arg Phe Thr Ile Ser Arg Asp Asp Ser Lys Ser Gly
65                  70                  75                  80 gtc tac ctg caa atg aac aac tta aga gct gag gac act ggc att tat     288
Val Tyr Leu Gln Met Asn Asn Leu Arg Ala Glu Asp Thr Gly Ile Tyr
                85                  90                  95 ttc tgt acc aag tta tca cta cgt tac tgg ttc ttc gat gtc tgg ggc     336
Phe Cys Thr Lys Leu Ser Leu Arg Tyr Trp Phe Phe Asp Val Trp Gly
            100                 105                 110 gca ggg acc acg gtc acc gtc tcc tca                                  363
Ala Gly Thr Thr Val Thr Val Ser Ser
        115                 120

<210> SEQ ID NO 2
<211> LENGTH: 121
<212> TYPE: PRT
<213> ORGANISM: mouse

<400> SEQUENCE: 2

Glu Leu Lys Leu Glu Glu Ser Gly Gly Gly Leu Val Gln Pro Gly Gly
```

```
              1               5                  10                 15
          Ser Met Lys Leu Ser Cys Ala Ala Ser Gly Phe Thr Phe Ser Asp Ala
                          20                  25                  30

Trp Met Asp Trp Val Arg Gln Ser Pro Glu Lys Gly Leu Glu Trp Ile
                          35                  40                  45

Ala Glu Ile Arg Ser Lys Ala Asn Asn Tyr Ala Thr Tyr Phe Ala Glu
                          50                  55                  60

Ser Val Lys Gly Arg Phe Thr Ile Ser Arg Asp Asp Ser Lys Ser Gly
          65                  70                  75                  80

Val Tyr Leu Gln Met Asn Asn Leu Arg Ala Glu Asp Thr Gly Ile Tyr
                          85                  90                  95

Phe Cys Thr Lys Leu Ser Leu Arg Tyr Trp Phe Phe Asp Val Trp Gly
                         100                 105                 110

Ala Gly Thr Thr Val Thr Val Ser Ser
                         115                 120

<210> SEQ ID NO 3
<211> LENGTH: 339
<212> TYPE: DNA
<213> ORGANISM: mouse
<220> FEATURE:
<221> NAME/KEY: CDS
<222> LOCATION: (1)..(339)

<400> SEQUENCE: 3 gat ttt gtg atg acc cag act cca ctc act ttg tcg gtt acc att gga       48
Asp Phe Val Met Thr Gln Thr Pro Leu Thr Leu Ser Val Thr Ile Gly
 1               5                  10                  15 caa cca gcc tcc atc tct tgc aag tca agt cag agc ctc ttg gat agt       96
Gln Pro Ala Ser Ile Ser Cys Lys Ser Ser Gln Ser Leu Leu Asp Ser
             20                  25                  30 gat gga aag aca tat ttg aat tgg ttg tta cag agg cca ggc cag tct      144
Asp Gly Lys Thr Tyr Leu Asn Trp Leu Leu Gln Arg Pro Gly Gln Ser
         35                  40                  45 cca aag cac ctc atc tat ctg gtg tct aaa ctg gac tct gga gtc cct      192
Pro Lys His Leu Ile Tyr Leu Val Ser Lys Leu Asp Ser Gly Val Pro
     50                  55                  60 gac agg ttc act ggc agt gga tca ggg acc gat ttc aca ctg aga atc      240
Asp Arg Phe Thr Gly Ser Gly Ser Gly Thr Asp Phe Thr Leu Arg Ile
65                  70                  75                  80 agc aga gtg gag gct gag gat ttg gga gtt tat tat tgc tgg caa agt      288
Ser Arg Val Glu Ala Glu Asp Leu Gly Val Tyr Tyr Cys Trp Gln Ser
                 85                  90                  95 aca cat ttt ccg tgg acg ttc ggt gga ggc acc aag ctg gaa atc aaa      336
Thr His Phe Pro Trp Thr Phe Gly Gly Gly Thr Lys Leu Glu Ile Lys
            100                 105                 110 cgg                                                                  339
Arg

<210> SEQ ID NO 4
<211> LENGTH: 113
<212> TYPE: PRT
<213> ORGANISM: mouse

<400> SEQUENCE: 4

Asp Phe Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
             20                  25                  30
```

```
Asp Gly Lys Thr Tyr Leu Asn Trp Leu Leu Gln Arg Pro Gly Gln Ser
            35                  40                  45

Pro Lys His Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Arg Ile
 65                  70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

Arg

<210> SEQ ID NO 5
<211> LENGTH: 420
<212> TYPE: DNA
<213> ORGANISM: Artificial Sequence
<220> FEATURE:
<223> OTHER INFORMATION: humanized antibody
<220> FEATURE:
<221> NAME/KEY: CDS
<222> LOCATION: (1)..(420)

<400> SEQUENCE: 5 atg tac ttg gga ctg aac tat gtt ttc atc gtt ttt ctc ctg aat ggt     48
Met Tyr Leu Gly Leu Asn Tyr Val Phe Ile Val Phe Leu Leu Asn Gly
 1               5                  10                  15 gtc cag agt gaa gtg cag ctt gtg gag tct gga gga ggc ttg gtg cag     96
Val Gln Ser Glu Val Gln Leu Val Glu Ser Gly Gly Gly Leu Val Gln
                20                  25                  30 cct gga gga tcc ctg aaa ctc tct tgt gct gcc tct gga ttc act ttt    144
Pro Gly Gly Ser Leu Lys Leu Ser Cys Ala Ala Ser Gly Phe Thr Phe
            35                  40                  45 agt gac gcc tgg atg gac tgg gtc cgc cag gct ccg gga agg ggg ctt    192
Ser Asp Ala Trp Met Asp Trp Val Arg Gln Ala Ser Gly Lys Gly Leu
 50                  55                  60 gag tgg att gct gaa att aga agc aaa gct aat aat tat gca aca tac    240
Glu Trp Ile Ala Glu Ile Arg Ser Lys Ala Asn Asn Tyr Ala Thr Tyr
 65                  70                  75                  80 ttt gct gag tct gtg aaa ggg agg ttc acc atc tca aga gat gat tcc    288
Phe Ala Glu Ser Val Lys Gly Arg Phe Thr Ile Ser Arg Asp Asp Ser
                85                  90                  95 aaa aac acc gcc tac ctg caa atg aac agc tta aaa acc gag gac act    336
Lys Asn Thr Ala Tyr Leu Gln Met Asn Ser Leu Lys Thr Glu Asp Thr
            100                 105                 110 gcc gtt tat tac tgt acc aag tta tca ctg cgt tac tgg ttc ttc gat    384
Ala Val Tyr Tyr Cys Thr Lys Leu Ser Leu Arg Tyr Trp Phe Phe Asp
115                 120                 125 gtc tgg ggc cag ggg acc ctg gtc acc gtc tcc tca                    420
Val Trp Gly Gln Gly Thr Leu Val Thr Val Ser Ser
130                 135                 140

<210> SEQ ID NO 6
<211> LENGTH: 140
<212> TYPE: PRT
<213> ORGANISM: Artificial Sequence
<220> FEATURE:
<223> OTHER INFORMATION: Synthetic Construct

<400> SEQUENCE: 6

Met Tyr Leu Gly Leu Asn Tyr Val Phe Ile Val Phe Leu Leu Asn Gly
 1               5                  10                  15
```

```
Val Gln Ser Glu Val Gln Leu Val Glu Ser Gly Gly Leu Val Gln
            20                  25                  30

Pro Gly Gly Ser Leu Lys Leu Ser Cys Ala Ala Ser Gly Phe Thr Phe
        35                  40                  45

Ser Asp Ala Trp Met Asp Trp Val Arg Gln Ala Ser Gly Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Asn Thr Ala Tyr Leu Gln Met Asn Ser Leu Lys Thr Glu Asp Thr
            100                 105                 110

Ala Val Tyr Tyr Cys Thr Lys Leu Ser Leu Arg Tyr Trp Phe Phe Asp
        115                 120                 125

Val Trp Gly Gln Gly Thr Leu Val Thr Val Ser Ser
    130                 135                 140

<210> SEQ ID NO 7
<211> LENGTH: 363
<212> TYPE: DNA
<213> ORGANISM: Artificial Sequence
<220> FEATURE:
<223> OTHER INFORMATION: humanized antibody
<220> FEATURE:
<221> NAME/KEY: CDS
<222> LOCATION: (1)..(363)

<400> SEQUENCE: 7 gaa gtg cag ctt gtg gag tct gga gga ggc ttg gtg cag cct gga gga        48
Glu Val Gln Leu Val Glu Ser Gly Gly Gly Leu Val Gln Pro Gly Gly
1               5                   10                  15 tcc ctg aaa ctc tct tgt gct gcc tct gga ttc act ttt agt gac gcc        96
Ser Leu Lys Leu Ser Cys Ala Ala Ser Gly Phe Thr Phe Ser Asp Ala
            20                  25                  30 tgg atg gac tgg gtc cgc cag gct tcc ggg aag ggg ctt gag tgg att       144
Trp Met Asp Trp Val Arg Gln Ala Ser Gly Lys Gly Leu Glu Trp Ile
        35                  40                  45 gct gaa att aga agc aaa gct aat aat tat gca aca tac ttt gct gag       192
Ala Glu Ile Arg Ser Lys Ala Asn Asn Tyr Ala Thr Tyr Phe Ala Glu
    50                  55                  60 tct gtg aaa ggg agg ttc acc atc tca aga gat gat tcc aaa aac acc       240
Ser Val Lys Gly Arg Phe Thr Ile Ser Arg Asp Asp Ser Lys Asn Thr
65                  70                  75                  80 gcc tac ctg caa atg aac agc tta aaa acc gag gac act gcc gtt tat       288
Ala Tyr Leu Gln Met Asn Ser Leu Lys Thr Glu Asp Thr Ala Val Tyr
                85                  90                  95 tac tgt acc aag tta tca ctg cgt tac tgg ttc ttc gat gtc tgg ggc       336
Tyr Cys Thr Lys Leu Ser Leu Arg Tyr Trp Phe Phe Asp Val Trp Gly
            100                 105                 110 cag ggg acc ctg gtc acc gtc tcc tca                                   363
Gln Gly Thr Leu Val Thr Val Ser Ser
        115                 120

<210> SEQ ID NO 8
<211> LENGTH: 121
<212> TYPE: PRT
<213> ORGANISM: Artificial Sequence
<220> FEATURE:
<223> OTHER INFORMATION: Synthetic Construct

<400> SEQUENCE: 8
```

```
Glu Val Gln Leu Val Glu Ser Gly Gly Gly Leu Val Gln Pro Gly
1               5                  10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Ile
            35                  40                  45

Ala Glu Ile Arg Ser Lys Ala Asn Asn Tyr Ala Thr Tyr Phe Ala Glu
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Lys Leu Ser Leu Arg Tyr Trp Phe Phe Asp Val Trp Gly
            100                 105                 110

Gln Gly Thr Leu Val Thr Val Ser Ser
            115                 120
```

<210> SEQ ID NO 9
<211> LENGTH: 396
<212> TYPE: DNA
<213> ORGANISM: Artificial Sequence
<220> FEATURE:
<223> OTHER INFORMATION: humanized antibody
<220> FEATURE:
<221> NAME/KEY: CDS
<222> LOCATION: (1)..(396)

<400> SEQUENCE: 9

```
atg atg agt cct gcc cag ttc ctg ttt ctg ttg gtg ctc tgg att cgg      48
Met Met Ser Pro Ala Gln Phe Leu Phe Leu Leu Val Leu Trp Ile Arg
1               5                  10                  15 gaa acc aac ggt gat atc gtg atg acc cag act cca ctc tct ttg tcc      96
Glu Thr Asn Gly Asp Ile Val Met Thr Gln Thr Pro Leu Ser Leu Ser
            20                  25                  30 gtt acc cct gga caa cca gcc tcc atc tct tgc aag tca agt cag agc     144
Val Thr Pro Gly Gln Pro Ala Ser Ile Ser Cys Lys Ser Ser Gln Ser
        35                  40                  45 ctc ttg gat agt gat gga aag aca tat ttg aat tgg ttg tta cag aag     192
Leu Leu Asp Ser Asp Gly Lys Thr Tyr Leu Asn Trp Leu Leu Gln Lys
    50                  55                  60 cca ggc cag tct cca cag cac ctc atc tat ctg gtg tct aaa ctg gac     240
Pro Gly Gln Ser Pro Gln His Leu Ile Tyr Leu Val Ser Lys Leu Asp
65                  70                  75                  80 tct gga gtc cct gac agg ttc agt ggc agt gga tca ggg acc gat ttc     288
Ser Gly Val Pro Asp Arg Phe Ser Gly Ser Gly Ser Gly Thr Asp Phe
                85                  90                  95 aca ctg aaa atc agc aga gtg gag gct gag gat gtt gga gtt tat tat     336
Thr Leu Lys Ile Ser Arg Val Glu Ala Glu Asp Val Gly Val Tyr Tyr
            100                 105                 110 tgc tgg caa agt aca cat ttt ccc tgg acc ttc ggt gga ggc acc aag     384
Cys Trp Gln Ser Thr His Phe Pro Trp Thr Phe Gly Gly Gly Thr Lys
        115                 120                 125 gtg gaa atc aaa                                                      396
Val Glu Ile Lys
    130
```

<210> SEQ ID NO 10
<211> LENGTH: 132
<212> TYPE: PRT
<213> ORGANISM: Artificial Sequence
<220> FEATURE:

<223> OTHER INFORMATION: Synthetic Construct

<400> SEQUENCE: 10

Met Met Ser Pro Ala Gln Phe Leu Phe Leu Leu Val Leu Trp Ile Arg
1               5                   10                  15

Glu Thr Asn Gly Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Lys
    50                  55                  60

Pro Gly Gln Ser Pro Gln His Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Ser Thr His Phe Pro Trp Thr Phe Gly Gly Gly Thr Lys
        115                 120                 125

Val Glu Ile Lys
    130

<210> SEQ ID NO 11
<211> LENGTH: 336
<212> TYPE: DNA
<213> ORGANISM: Artificial Sequence
<220> FEATURE:
<223> OTHER INFORMATION: humanized antibody
<220> FEATURE:
<221> NAME/KEY: CDS
<222> LOCATION: (1)..(336)

<400> SEQUENCE: 11

```
gat atc gtg atg acc cag act cca ctc tct ttg tcc gtt acc cct gga        48
Asp Ile Val Met Thr Gln Thr Pro Leu Ser Leu Ser Val Thr Pro Gly
1               5                   10                  15 caa cca gcc tcc atc tct tgc aag tca agt cag agc ctc ttg gat agt        96
Gln Pro Ala Ser Ile Ser Cys Lys Ser Ser Gln Ser Leu Leu Asp Ser
            20                  25                  30 gat gga aag aca tat ttg aat tgg ttg tta cag aag cca ggc cag tct       144
Asp Gly Lys Thr Tyr Leu Asn Trp Leu Leu Gln Lys Pro Gly Gln Ser
        35                  40                  45 cca cag cac ctc atc tat ctg gtg tct aaa ctg gac tct gga gtc cct       192
Pro Gln His Leu Ile Tyr Leu Val Ser Lys Leu Asp Ser Gly Val Pro
    50                  55                  60 gac agg ttc agt ggc agt gga tca ggg acc gat ttc aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt gga gtt tat tat tgc tgg caa agt       288
Ser Arg Val Glu Ala Glu Asp Val Gly Val Tyr Tyr Cys Trp Gln Ser
                85                  90                  95 aca cat ttt ccc tgg acc ttc ggt gga ggc acc aag gtg gaa atc aaa       336
Thr His Phe Pro Trp Thr Phe Gly Gly Gly Thr Lys Val Glu Ile Lys
            100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: Synthetic Construct

```
<400> SEQUENCE: 12

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
                100                 105                 110

<210> SEQ ID NO 13
<211> LENGTH: 112
<212> TYPE: PRT
<213> ORGANISM: Artificial Sequence
<220> FEATURE:
<223> OTHER INFORMATION: humanized antibody

<400> SEQUENCE: 13

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
                100                 105                 110
```